(12) United States Patent
Gazit et al.

(10) Patent No.: US 6,849,255 B2
(45) Date of Patent: Feb. 1, 2005

(54) METHODS AND COMPOSITIONS FOR ENHANCING CARTILAGE REPAIR

(75) Inventors: Dan Gazit, Jerusalem (IL); Yoram Zilberman, Jerusalem (IL); Gadi Turgeman, Jerusalem (IL); Gadi Pelled, Rishon Leziyon (IL); Gerhard Gross, Braunschweig (DE); Stefan Czichos, Peine (DE); Andrea Hoffmann, Hannover (DE)

(73) Assignees: Yissum Research Development Company of the Hebrew University of Jerusalem, Jerusalem (IL); Gesellschaft Fuer Biotechnologische Forschung MBH, Braunschweig (DE)

( * ) Notice: Subject to any disclaimer, the term of this patent is extended or adjusted under 35 U.S.C. 154(b) by 270 days.

(21) Appl. No.: 10/067,980

(22) Filed: Feb. 8, 2002

(65) Prior Publication Data

US 2003/0185807 A1 Oct. 2, 2003

Related U.S. Application Data

(63) Continuation-in-part of application No. 09/376,276, filed on Aug. 18, 1999, now abandoned.

(30) Foreign Application Priority Data

Aug. 18, 1998 (DE) .......................... 198 37 438

(51) Int. Cl.[7] .................. A61K 48/00; A61K 31/70; C12N 15/63; C12N 5/08
(52) U.S. Cl. ................. 424/93.21; 435/455; 435/320.1; 514/44
(58) Field of Search .................. 424/93.21; 514/44; 435/455, 320.1

(56) References Cited

U.S. PATENT DOCUMENTS

| 5,013,649 A | 5/1991 | Wang et al. |
| 5,106,748 A | 4/1992 | Wozney et al. |
| 5,108,922 A | 4/1992 | Wang et al. |
| 5,116,738 A | 5/1992 | Wang et al. |
| 5,141,905 A | 8/1992 | Rosen et al. |
| 5,187,076 A | 2/1993 | Wozney et al. |
| 5,639,638 A | 6/1997 | Wozney et al. |

FOREIGN PATENT DOCUMENTS

| DE | 19837438 | 8/1998 |
| WO | 91/18098 | 11/1991 |
| WO | 93/00050 | 1/1993 |
| WO | 93/00432 | 1/1993 |

OTHER PUBLICATIONS

Gafni et al. Stem cells as vehicles for orthopedic gene therapy. Gene therapy 11:417–426, 2004.*
Hoffmann et al. The T–box transcription factor Brachyury mediates cartilage development in mesenchymal stem cell line C3H10T1/2. J. Cell Science 115:769–781, 2002.*
Smith, J. T–box genes—what they do and how they do it. TIG 15: 154–158, 1999.*
Papaioannou et al. The T–box gene family. BioEssays 20:9–19, 1998.*
Brittberg M et al (1994) N Engl J Med. 331(14):889–95.
Kispert A et al, (1995) EMBO J. Oct. 2, 1995;14(19):4763–72.
Papaioannou VE et al (1998) Bioessays. 20(1):9–19.
Smith (1999) J Trends Genet. 15(4):154–8.
Ahrens (1993) DNA Cell Biol. 12(10):871–80.
Hollnagel A et al, (1997) J Bone Miner Res. 12(12):1993–2004.
Bachner D et al (1998) Dev Dyn. 213(4):398–411.
Bachner D et al (1998) Mech Dev. 84(1–2):121–5.
Zehentner BM et al (1999) J Bone Miner Res. 14(10):1734–41.
Murakami et al (2000) Proc Natl Acad Sci U S A. 97(3):1113–8.
Kispert A et al, (1995) Dev Biol. 168(2):406–15.
Takeuchi et al (2000) Genes Cells 5, 71–78.
Mazars A et al (2000) Oncogene. Mar 2;19(10):1277–87.
Kispert A et al (1994) Dev Biol. Jan;161(1): 179–93.
Wilkinson DG et al (1990) Nature. 343(6259)657–9.

* cited by examiner

*Primary Examiner*—David Guzo
*Assistant Examiner*—Quang Nguyen
(74) *Attorney, Agent, or Firm*—Eithan, Pearl, Latzer & Cohen Zedek, LLP; Mark S. Cohen

(57) ABSTRACT

The invention relates to methods of enhancing repair of a cartilage and/or inducing formation of a cartilage by administering a cell which expresses a factor of the T-box family, which includes inter-alia the brachyury. In another embodiment, the invention relates to an engineered cell, which is transfected with a vector comprising a nucleic acid sequence encoding a factor of the T-box family, thereby expressing a factor of the T-box family. In another embodiment, the invention relates to compositions comprising a vector which comprises a nucleic acid sequence encoding a factor of the T-box family and in another embodiment the composition comprising cell which expresses a factor of the T-box family, which includes inter-alia the brachyury.

9 Claims, 11 Drawing Sheets

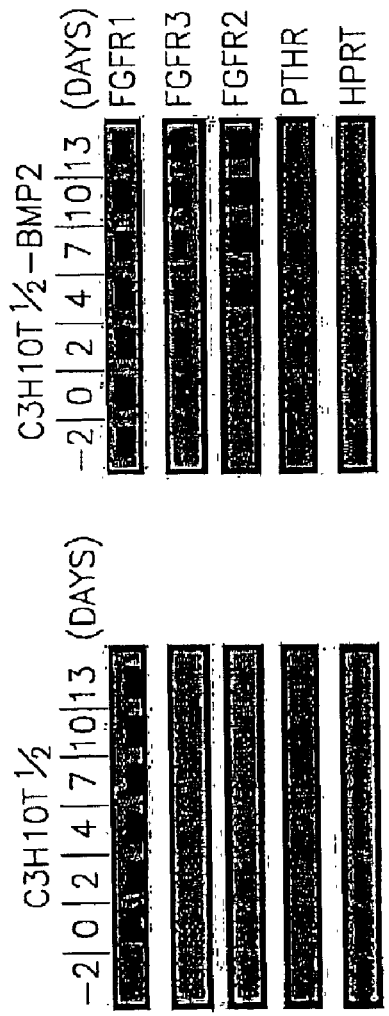
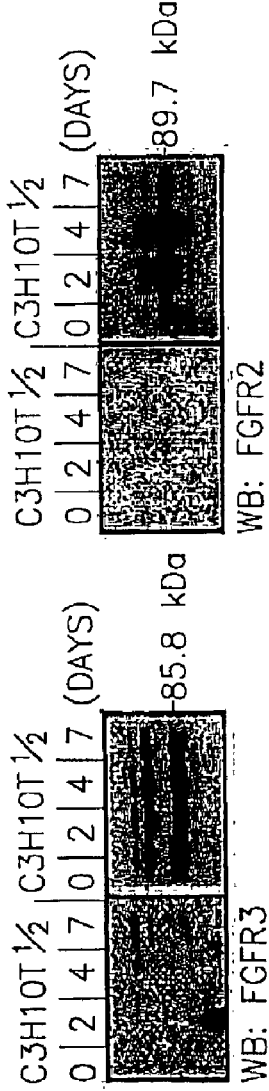
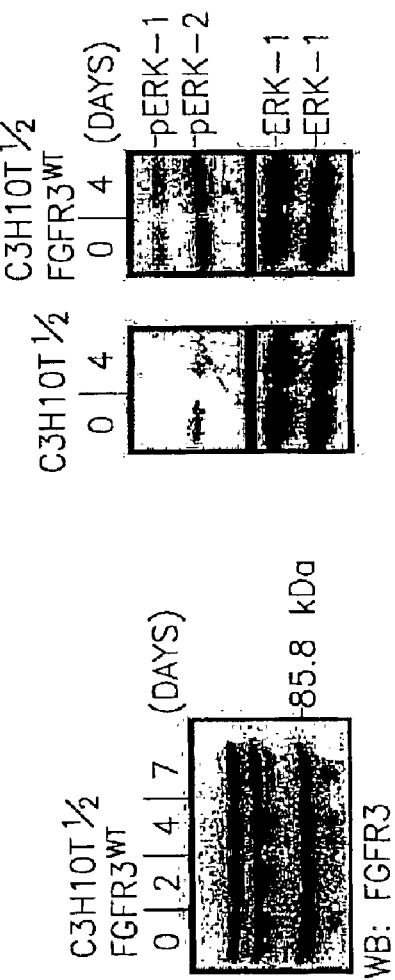
FIG.1A
FIG.1B
FIG.1C

C3H10T½–BMP2  C3H10T½–BMP2 Brachyury alcian Blue, day 11

20 days, HE

SEQUENCE LISTING

<160> NUMBER OF SEQ ID NOS: 17

<210> SEQ ID NO 1
<211> LENGTH: 19
<212> TYPE: DNA
<213> ORGANISM: Mus musculus

<400> SEQUENCE: 1
gctggtgaaa aggacctct                                                    19

<210> SEQ ID NO 2
<211> LENGTH: 20
<212> TYPE: DNA
<213> ORGANISM: Mus musculus

<400> SEQUENCE: 2
aagtagatgg ccacaggact                                                   20

<210> SEQ ID NO 3
<211> LENGTH: 17
<212> TYPE: DNA
<213> ORGANISM: Mus musculus

<400> SEQUENCE: 3
gccctgcctg cttcgtg                                                      17

<210> SEQ ID NO 4
<211> LENGTH: 20
<212> TYPE: DNA
<213> ORGANISM: Mus musculus

<400> SEQUENCE: 4

-continued cgtaagttgg aatggttttt                                                  20

<210> SEQ ID NO 5
<211> LENGTH: 21
<212> TYPE: DNA
<213> ORGANISM: Mus musculus

<400> SEQUENCE: 5
cctgtctgct tcttgtaaaa c                                                21

<210> SEQ ID NO 6
<211> LENGTH: 20
<212> TYPE: DNA
<213> ORGANISM: Mus musculus

<400> SEQUENCE: 6
agcatctgta ggggtcttct                                                  20

<210> SEQ ID NO 7
<211> LENGTH: 20
<212> TYPE: DNA
<213> ORGANISM: Mus musculus

<400> SEQUENCE: 7
gcagacctag cagacaccat                                                  20

<210> SEQ ID NO 8
<211> LENGTH: 21
<212> TYPE: DNA
<213> ORGANISM: Mus musculus

<400> SEQUENCE: 8
gagctgctgt gacatccata c                                                21

<210> SEQ ID NO 9
<211> LENGTH: 24
<212> TYPE: DNA
<213> ORGANISM: Mus musculus

<400> SEQUENCE: 9
gttgccatca tatactgttt ctgc                                             24

<210> SEQ ID NO 10
<211> LENGTH: 21
<212> TYPE: DNA
<213> ORGANISM: Mus musculus

<400> SEQUENCE: 10
ggcttcttgg tccatctgtc c                                                21

<210> SEQ ID NO 11
<211> LENGTH: 22
<212> TYPE: DNA
<213> ORGANISM: Mus musculus

<400> SEQUENCE: 11
cctgcgcagt cccccaaaga ag                                               22

<210> SEQ ID NO 12
<211> LENGTH: 22
<212> TYPE: DNA
<213> ORGANISM: Mus musculus

```
<400> SEQUENCE: 12
ctgcaggcat caaaggagta gt                                               22

<210> SEQ ID NO 13
<211> LENGTH: 23
<212> TYPE: DNA
<213> ORGANISM: Mus musculus

<400> SEQUENCE: 13
ttggaggatg ggccggtgtg gtg                                              23

<210> SEQ ID NO 14
<211> LENGTH: 22
<212> TYPE: DNA
<213> ORGANISM: Mus musculus

<400> SEQUENCE: 14
gcgcttcatc tgcctggtct tg                                               22

<210> SEQ ID NO 15
<211> LENGTH: 24
<212> TYPE: DNA
<213> ORGANISM: pMT7T3

<400> SEQUENCE: 15
ttagtctttt tgtcttttat ttca                                             24

<210> SEQ ID NO 16
<211> LENGTH: 24
<212> TYPE: DNA
<213> ORGANISM: PMT7T3-3'

<400> SEQUENCE: 16
gatcgaagct caattaaccc tcac                                             24

<210> SEQ ID NO 17
<211> LENGTH: 24
<212> TYPE: DNA
<213> ORGANISM: Mus musculus

<400> SEQUENCE: 17
aatttcacac ctaggtgtga aatt                                             24
```

METHODS AND COMPOSITIONS FOR ENHANCING CARTILAGE REPAIR

This application is a Continuation-in part Application of U.S. Ser. No. 09/376,276, filed Aug. 18, 1999, now abandoned which claims priority from DE Application No. 198.37.438.0, filed Aug. 18, 1998, which are both incorporated herein by reference.

FIELD OF THE INVENTION

The invention relates to methods of enhancing repair of a cartilage and/or inducing formation of a cartilage by administering a cell which expresses at least one factor of the T-box family, which includes inter-alia the brachyury. In another embodiment, the invention relates to an engineered cell, which is transfected with a vector comprising at least one nucleic acid sequence encoding a factor of the T-box family, thereby expressing at least one factor of the T-box family. In another embodiment, the invention relates to compositions comprising a vector which comprises at least one nucleic acid sequence encoding a factor of the T-box family and in another embodiment the composition comprising cell which expresses at least one factor of the T-box family, which includes inter-alia the brachyury.

BACKGROUND OF THE INVENTION

The meniscus, fibrocartilaginous tissue found within the knee joint, is responsible for shock absorption, load transmission, and stability within the knee joint. According to the National Center for Health Statistics, over 600,000 surgeries each year are the result of complications with the meniscus. The meniscus has the intrinsic ability to heal itself; unfortunately, this property is limited only to the vascular portions of the tissue. For damage outside of these areas and overall degeneration of the tissue, methods need to be developed that will assist the meniscus in healing itself Sweigart M A Tissue Eng 7(2), 111–29 (April 2001).

Degeneration of articular cartilage in osteoarthritis is a serious medical problem caused by arthritis, both rheumatoid and osteoarthritis. Drugs are given to control the pain and to keep the swelling down, but the cartilage continues to be destroyed. Eventually, the joint must be replaced. It is still unknown why cartilage does not heal and no solutions to this problem are known Mankin, N. E. J. Med. 331(14), 940–941 (October 1994). Soon after superficial injury, chondrocytes adjacent to the injured surfaces show a brief burst of mitotic activity associated with an increase in glycosaminoglycan and collagen synthesis. Despite these attempts at repair, there is no appreciable increase in the bulk of cartilage matrix and the self repair process is usually ineffective in healing the defects.

Osteochondral, or full-thickness, cartilage defects expand into the subchondral bone. Such defects arise after the detachment of osteochondritic dissecting flaps, fractured osteochondral fragments, or from chronic wear of degenerative articular cartilage. Osteochondral defects depend on the extrinsic mechanism for repair. Extrinsic healing relies on mesenchymal elements from subchondral bone to participate in the formation of new connective tissue. This fibrous tissue may or may not undergo metaplastic changes to form fibrocartilage. Even if fibrocartilage is formed, it does not display the same biochemical composition or mechanical properties of normal articular cartilage or subchondral bone and degenerates with use, Furukawa, et al., J. Bone Joint Surg. 62A, 79 (1980); Coletti, et al., J. Bone Joint Surg. 54A, 147 (1972); Buckwalter, et al., "Articular cartilage: composition, structure, response to injury and methods of facilitating repair", in Articular Cartilage and Knee Joint Function: Basic Science and Arthroscopy, Ewing J E, Ed., (New York, Raven Press, 1990), 19.

Injection of dissociated chondrocytes directly into the site of the defect has also been described as a means for forming new cartilage, as reported by Brittberg, et al., N. E. J. Med. 331, 889–895 (October 1994). Cartilage was harvested from minor load-bearing regions on the upper medial femoral condyle of the damaged knee, cultured, and implanted two to three weeks after harvesting.

Moreover, if the defect includes a part of the underlying bone, this is not corrected by the use of chondrocytes. The bone is required to support the new cartilage.

Cartilage grafts are also needed in plastic surgery like in rhinoplasty, and the reconstruction of ears.

The possibility of using stem cells was also examined. Stem cells are cells which are not terminally differentiated, which can divide without limit, and divide to yield cells that are either stem cells or which irreversibly differentiate to yield a new type of cell. Unfortunately, there is no known specific inducer of the mesenchymal stem cells that yields only cartilage. In vitro studies in which differentiation is achieved using different bioactive factors or molecules, yields differentiation of the cells to cartilage which eventually calcified and turned into bone.

Thus, there is a need to have a method and composition for the formation or repair of a cartilage or a bone. In another embodiment, it will be highly advantageous to have a cell which can divide and form a cartilage or a bone tissue.

SUMMARY OF THE INVENTION

In one embodiment the invention provides a method of enhancing repair of a cartilage comprising the step of administering to a subject an effective amount of a cell which expresses at least one factor of the T-box family, thereby enhancing repair of the cartilage.

In another embodiment the invention provides a method of inducing formation of a cartilage comprising the step of administering to a subject an effective amount of a cell which expresses at least one factor of the T-box family, thereby inducing formation of the cartilage.

In another embodiment the invention provides a method of enhancing repair of a cartilage in the body comprising the step of administrating a recombinant vector which comprises a nucleic acid encoding a factor of the T-box family to the cartilage of a subject, thereby enhancing repair of the cartilage.

In another embodiment the invention provides a method of inducing formation of a cartilage in the body comprising the step of administrating a recombinant vector which comprises a nucleic acid encoding a factor of the T-box family to the cartilage of a subject, thereby inducing formation of the cartilage.

In another embodiment the invention provides a method of inducing chondrocyte differentiation comprising the step of administering of a recombinant vector which comprises a nucleic acid encoding a factor of the T-box family, thereby inducing chondrocyte formation.

In another embodiment the invention provides a method of repairing or forming a cartilage in a subject in need comprising the steps of: obtaining a cell from of the subject;

transfecting said cell with a recombinant vector comprising a nucleic acid sequence encoding a factor of the T-box family, so as to obtain an engineered cell which expresses a factor of the T-box family; and administering said engineered cell to the subject.

In another embodiment the invention provides a method for the production of transplantable cartilage matrix, the method comprising the steps of: obtaining a cell; transfecting said cell with a recombinant vector comprising a nucleic acid sequence encoding a factor of the T-box family, so as to obtain an engineered cell which expresses a factor of the T-box family; and culturing said cell with the cell-associated matrix for a time effective for allowing formation of a transplantable cartilage matrix.

In another embodiment the invention provides an engineered cell which expresses a factor of the T-box family.

In another embodiment the invention provides an implant device comprising at least one engineered cell which expresses a factor of the T-box family and a pharmaceutically acceptable carrier.

In another embodiment the invention provides a composition comprising an engineered cell which expresses a factor of the T-box family and a pharmaceutically acceptable carrier.

In another embodiment the invention provides a composition comprising at least one recombinant vector which comprises a nucleic acid sequence encoding at least one factor of the T-box family and a pharmaceutically acceptable carrier.

BRIEF DESCRIPTION OF THE DRAWINGS

FIG. 1. FGFR3 mediates chondrocytic differentiation in mesenchymal stem cell line C3H10T1/2. FIG. 1a shows the RT-PCR analyses of BMP2-dependent expression of FGF- and PTH/PTHrP-receptors in mesenchymal stem cell line C3H10T1/2 in the presence or absence of recombinantlly expressed BMP2. FIG. 1b shows the effect of cyclohexamide pretreatment of C3H10T1/2 cells. Cycloheximide pretreatment of C3H10T1/2 cells does not prevent BMP-induction of the FGFR3 gene. Cells were mock-treated (control) or were treated with BMP2 (50 ng/ml). FIG. 1c demonstrates western immunoblotting for the detection of BMP2-dependent FGFR3 and FGFR2 expression in cellular extracts of C3H10T1/2 lines. FIG. 1e demonstrates that the forced expression of FGFR3 in parental C3H10T1/2 cells is sufficient for the induction of the chondrogenic lineage.

FIG. 2. The T-box transcription factor Brachyury mediates chondrogenic differentiation in MSCs in vitro and ectopically in vivo. FIG. 2a lower panel: western immunoblotting of recombinant HA-tagged Brachyury (aa 1–436) in cellular extracts of C3H10T1/2 (C3H10T1/2-Brachyury) with HA-antibody SC-805 (Santa Cruz) Brachyury has been constitutively expressed under the control of the murine PGK-promoter. Expression of Brachyury is indicated (triangle). Molecular weight marker (M) shown is ovalbumin (43 kDa).

FIG. 3. Dominant-negative Brachyury (dnBrachyury; T-box domain) blocks BMP2-mediated chondrogenic development in C3H10T1/2 MSCs in vitro and ectopically in vivo.

FIG. 4. Dominant-negative FGFR3 (dnFGFR3) interferes with osteo-/chondrogenic development, with FGFR2- and with Brachyury-expression in C3H10T1/2-BMP2.

FIG. 5. FGFR3 and Brachyury are involved in an auto-regulatory loop. FIG. 5a shows RT-PCR analyses of FGFR3 and Brachyury mRNA levels in mesenchymal progenitors C3H10T1/2 expressing recombinant FGFR3 (C3H10T1/2-FGFR3) or Brachyury (C3H10T1/2-Brachyury). FIG. 5b shows that Smad1-signaling is not sufficient for Brachyury and FGFR3 but for osteocalcin expression. RT-PCR analyses of FGFR3 and Brachyury mRNA levels in mesenchymal progenitors C3H10T1/2 expressing the biologically active Smad1-MH2 domain (C3H10T1/2-Smad1-MH2).

DETAILED DESCRIPTION OF THE EMBODIMENTS

Figure 1D:
FIG. 1d left panel: western immunoblotting to demonstrate the forced expression of FGFR3 in mesenchymal progenitors C3H10T1/2; right panel: the recombinant expression of FGFR3 in C3H10T1/2 leads to enhanced levels of activated MAP-kinases pERK-1 and pERK-2 during cultivation. Cell lysates were prepared 0 (=confluence) and 4 days post-confluence.
Figure 1D:
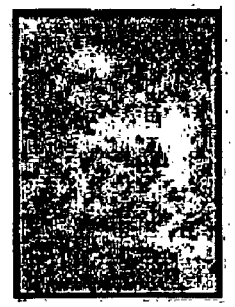
Figure 1D:
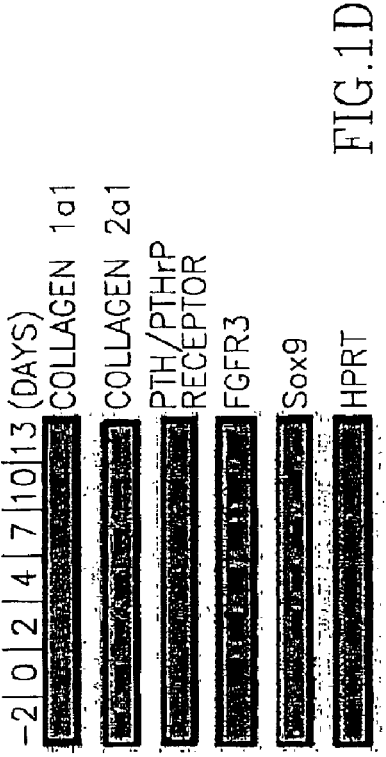
Figure 1D:
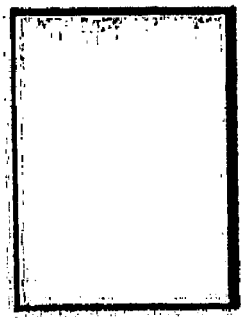
Figure 1D:
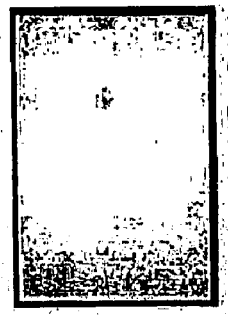
Figure 1D:
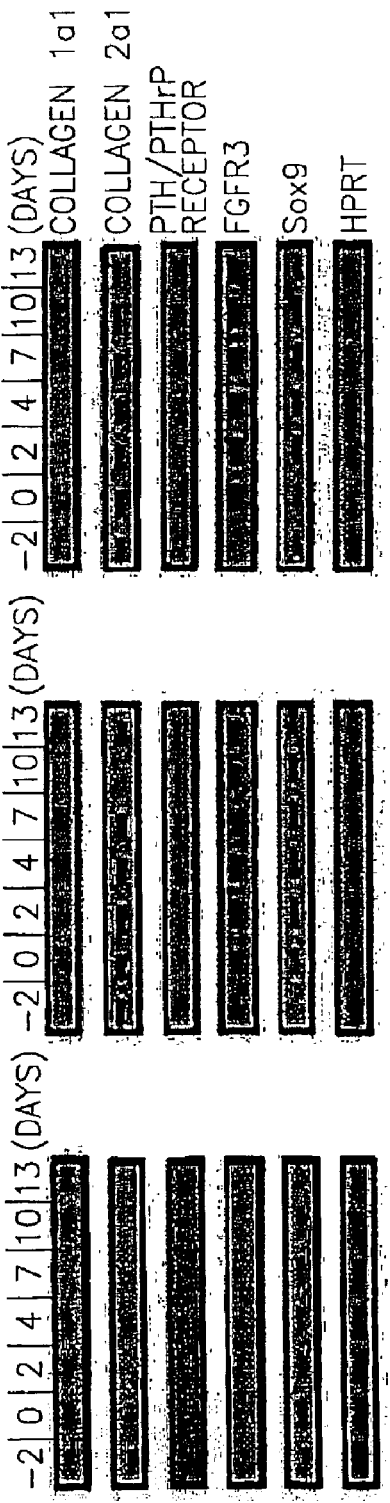

The invention relates to methods of enhancing repair of a cartilage and/or inducing formation of a cartilage by administering a cell which expresses a factor of the T-box family, which includes inter-alia the brachyury. In another embodiment, the invention relates to an engineered cell, which is transfected with a vector comprising a nucleic acid sequence encoding a factor of the T-box family, thereby expressing a factor of the T-box family. In another embodiment, the invention relates to compositions comprising a vector which comprises a nucleic acid sequence encoding a factor of the T-box family and in another embodiment the composition comprising cell which expresses a factor of the T-box family, which includes inter-alia the brachyury.

The term "cartilage" refers hereinabove to a specialized type of dense connective tissue consisting of cells embedded in a matrix. There are several kinds of cartilage. Translucent cartilage having a homogeneous matrix containing collagenous fibers is found in articular cartilage, in costal cartilages, in the septum of the nose, in larynx and trachea. Articular cartilage is hyaline cartilage covering the articular surfaces of bones. Costal cartilage connects the true ribs and the sternum. Fibrous cartilage contains collagen fibers. Yellow cartilage is a network of elastic fibers holding cartilage cells which is primarily found in the epiglottis, the external ear, and the auditory tube. Cartilage is tissue made up of extracellular matrix primarily comprised of the organic compounds collagen, hyaluronic acid (a proteoglycan), and chondrocyte cells, which are responsible for cartilage production. Collagen, hyaluronic acid and water entrapped within these organic matrix elements yield the unique elastic properties and strength of cartilage.

As used herein, "hyaline cartilage" refers to the connective tissue covering the joint surface. By way of example only, hyaline cartilage includes, but is not limited to, articular cartilage, costal cartilage, and nose cartilage.

As used herein, the term "enhancing cartilage repair" refers to healing and regeneration of cartilage injuries, tears, deformities or defects, and prophylactic use in preventing damage to cartilaginous tissue.

As used herein, the term "inducing formation" refers to the use in cartilage renewal or regeneration so as to ameliorate conditions of cartilage, degeneration, depletion or damage such as might be caused by aging, genetic or infectious disease, accident or any other cause, in humans, livestock, domestic animals or any other animal species. In another embodiment the formation of a cartilage is required for cartilage development in livestock, domestic animals or any other animal species in order to achieve increased growth for commercial or any other purpose. In another embodiment the formation of a cartilage is required in plastic surgeries, such as without being limited facial reconstruction in order to obtain a stabilized shape.

In one embodiment there is provided a recombinant vector comprising a nucleic acid sequence encoding a factor of the T-box family.

The term "T-box family" defined as a family of transcription factors that share the T-box, a 200 amino acid DNA-binding domain. The T-box family have been identified in both vertebrates and in vertebrates and plays a key role in embryonic development.

In another embodiment, the vector comprising a nucleic acid which encodes for Brachyury, or T, which refers hereinabove to the founder factor of the T-box family. It has been shown that Brachyury is highly expressed during gastrulation where it plays a decisive role in the generation of undifferentiated mesoderm and, thereafter, Brachyury expression is downregulated (reviewed in (Papaioannou and Silver, 1998; Smith, 1999).

The immediate BMP2-dependent upregulation of FGFR3 in MSCs (C3H10T1/2) and the inherent capacity of this receptor to initiate chondrogenic development in these cells prompted a screen for FGFR3-regulated transcription factors. The chondrogenic potential of Brachyury after recombinant expression in wild-type C3H10T1/2 cells (see below) has been hypothesized after it was shown, by the use of a subtractive screening method, exemplified in Example 1 that, among the transcription factors tested, the T-box transcription factor Brachyury was upregulated in FGFR3-expressing C3H10T1/2 cells (see also FIG. 5a).

As used herein, the term "nucleic acid" refers to polynucleotides or to ologonucleotides such as deoxyribonucleic acid (DNA), and, where appropriate, ribonucleic acid (RNA) or mimetics thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

The terms "protein", "polypeptide" and "peptide" are used interchangably herein when referring to a gene product.

The vector molecule can be any molecule capable of being delivered and maintained within the target cell or tissue such that the gene encoding the product of interest can be stably expressed. The vector molecule preferably utilized in the present invention is either a viral or retroviral vector molecule or a plasmid DNA non-viral molecule. This method preferably includes introducing the gene encoding the product into the cell of the mammalian connective tissue for a therapeutic or prophylactic use. Unlike previous pharmacological efforts, the methods of the present invention employ gene therapy to address the chronic debilitating effects of joint pathologies. The viral vectors used in the methods of the present invention can be selected form the group consisting of (a) a retroviral vector, such as MFG or pLJ; (b) an adeno-associated virus; (c) an adenovirus; and (d) a herpes virus, including but not limited to herpes simplex 1 or herpes simples 2 or (e)lentivirus. Alternatively, a non-viral vector, such as a DNA plasmid vector, can be used. Any DNA plasmid vector known to one of ordinary skill in the art capable of stable maintenance within the targeted cell or tissue upon delivery, regardless of the method of delivery utilized is within the scope of the present invention. Non-viral means for introducing the gene encoding for the product into the target cell are also within the scope of the present invention. Such non-viral means can be selected from the group consisting of (a) at least one liposome, (b) $Ca_3(PO_4)_2$, (c) electroporation, (d) DEAE-dextran, and (e) injection of naked DNA.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared with the wild type sequence, while the sequence still encodes a protein or peptide, or fragments thereof, that retain their wild type function despite these variations. Proteins, protein fragments, peptides, or derivatives also can experience deviations from the wild type from which still functioning in the same manner as the wild type form. Similarly, derivatives of the genes and products of interest used in the present invention will have the same biological effect on the host as the non-derivatized forms. Examples of such derivatives include but are not limited to dimerized or oligomerized forms of the genes or proteins, as wells as the genes or proteins modified by the addition of an immunoglobulin (Ig) group. Biologically active derivatives and fragments of the genes, DNA sequences, peptides and proteins of the present invention are therefore also within the scope of this invention. In addition, any nucleic acid which is cis acting and integrated upstream to an endogenous factor of the T-box family nucleic acid sequence is relevant to the present invention.

The term "cis-acting" is used to describe a genetic region that serves as an attachment site for DNA-binding proteins (e.g. enhancers, operators and promoters) thereby affecting the activity of genes on the same chromosome.

It was shown that Brachyury expression is upregulated by certain factor such as BMP2 and/or FGF3 (see FIGS. 4 and 5). Thus, in another embodiment, the vector of the invention further comprising a nucleic acid which encodes to a protein which activated the BMP signaling pathway. In another embodiment, the protein which activated the BMP signaling pathway is a member of the BMP family. In another embodiment the BMP is a BMP2. In another embodiment the vector further comprising a nucleic acid for fibroblast growth factor namely FGF-3.

The term "protein which activates BMP mediated signaling pathway" is defined hereinabove as a protein that can activate the BMP receptors, or the signaling cascade down stream of the receptor to elicit BMP specific cellular response. Examples, without being limited are members of the BMP family, such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076, and 5,141,905; BMP-8, disclosed in PCT publication W091/18098; BMP-9, disclosed in PCT publication W093/00432; and BMP-10 or BMP-11, disclosed in co-pending patent applications, Ser. No. 08/061,695 presently abandoned, a continuation-in-part of which has issued as U.S. Pat. No. 5,637,480, and 08/061,464 presently abandoned, a continuation-in-part of which has issued as U.S. Pat. No. 5,639,638 filed on May 12, 1993.

In another embodiment, there is provided an engineered cell which expresses at least one factor of the T-box family.

The term "engineered cell" is defined hereinabove to a cell or to a tissue which had been genetically modified and is expressing a factor of the T-box family or in another embodiment, increased amounts of the factor of the T-box family or in another embodiment express Brachury. The term "increased amount of the factor or the at least one factor of the T-box family refers hereinabove to at least 10 times more than normal.

The cell of the invention can be any cell. In one embodiment, it is a mammalian cell. In another embodiment, it is a mesenchymal stem cell, in another embodiment it is a progenitor cell, in another embodiment it is a cell derived from a cartilage. In another embodiment the cell can be derived from a fibroblast cell line, a mesenchymal cell line, a chondrocyte cell line, an osteoblast cell line, or an osteocyte cell line. The fibroblast cell line may be a human foreskin fibroblast cell line or NIH 3T3 cell line. In another embodiment the cell of the invention is a synovial cell or a synoviocyte. Synoviocytes are found in joint spaces adjacent to cartilage have an important role in cartilage metabolism. Synoviocytes produce metallo-proteinases, such as collagenases that are capable of breaking-down cartilage.

Stem cells are defined as cells which are not terminally differentiated, which can divide without limit, and divides to yield cells that are either stem cells or which irreversibly differentiate to yield a new type of cell. Those stem cells which give rise to a single type of cell are call unipotent cells; those which give rise to many cell types are called pluripotent cells. Chondro/osteoprogenitor cells, which are bipotent with the ability to differentiate into cartilage or bone, were isolated from bone marrow (for example, as described by Owen, J. Cell Sci. Suppl. 10, 63–76 (1988) and in U.S. Pat. No. 5,226,914 to Caplan, et al.).

It is important to note that mesenchymal stem cells and progenitors can be isolated from different source tissues, skin, bone marrow, muscle, and liver. In addition any cell type with stem cell properties or demonstrating differentiation plasticity for example without limitation, SP cells from the source of bone marrow, muscle, spleen or any other tissue.

Chondrogenic cells useful in the practice of the invention may be isolated from essentially any tissue containing chondrogenic cells. As used herein, the term "chondrogenic cell" is understood to mean any cell which, when exposed to appropriate stimuli, may differentiate into a cell capable of producing and secreting components characteristic of cartilage tissue. The chondrogenic cells may be isolated directly from pre-existing cartilage tissue, for example, hyaline cartilage, elastic cartilage, or fibrocartilage. Specifically, chondrogenic cells may be isolated from articular cartilage (from either weight-bearing or non-weight-bearing joints), costal cartilage, nasal cartilage, auricular cartilage, 30 tracheal cartilage, epiglottic cartilage, thyroid cartilage, arytenoid cartilage and cricoid cartilage. The cell from the cartilage can be derived from another animal, or another subject or in another embodiment, the cell of the cartilage or the bone can be derived from the subject in need.

In another embodiment, the cell further express at least one protein which activates BMP mediated signaling pathway or a FGF protein.

The expression of the at least one factor of the T-box family in combination with either and BMP or FGF or both in the cell can be due to the presence of two or more different vectors (trans vectors) or due to the expression of one vector which comprises two or more different nucleic acid sequences, which encode for the at least one member of the T-box family, the FGF and for at least one protein which activates the BMP mediated signaling pathway.

In another embodiment the invention provides complex tissue engineering. This term refers to engineering a cell with different nucleic acid sequences, wherein each sequence encodes to a specific pathway of differentiation. As such, the cell of the invention can be engineered to differentiate to an osteoblast as well as to a chondrocyte.

In another embodiment there is provided a composition comprising recombinant vector comprising a nucleic acid sequence encoding the a factor of the T-box family and a pharmaceutically acceptable carrier. It should be noted that the term "a nucleic acid sequence encoding the a factor of the T-box family" refers hereinabove to "at least one nucleic acid sequence encoding the at least one factor of the T-box family". Similarly the term "a cell" refers to "at least one cell".

In another embodiment, there is provided a composition comprising at least one engineered cell, wherein said engineered cell expresses least one factor of the T-box family at least one protein and a pharmaceutically acceptable carrier.

In another embodiment the composition can be a pharmaceutical composition.

Compositions of the invention may further comprise additional proteins, such as additional factors. These compositions may be used to induce the formation or repair of cartilage tissue.

The compositions of the invention may comprise, also BMP-12 or VL-1 (BMP-13), other therapeutically useful agents including MP52, epidermal growth factor (EGF), fibroblast growth factor (FGF), platelet derived growth factor (PDGF), transforming growth factors (TGF-α and TGF-β), and fibroblast growth factor-4 (FGF-4), parathyroid hormone (PTH), leukemia inhibitory factor (LIF/HILDA/DIA), insulin-like growth factors (IGF-I and IGF-II). Portions of these agents may also be used in compositions of the present invention. N another embodiment the composition comprises anti-inflammatory agents such as IL1 receptor antagonists, or IL4 or IL10 agonists.

In another embodiment, there is provided an implant device for transplantation in a subject in need comprising an engineered cell which expresses a factor of the T-box family and a pharmaceutically acceptable carrier. Cartilage implants are often used in reconstructive or plastic surgery such as rhinoplasty.

The preparation and formulation of such pharmaceutically/physiologically acceptable protein compositions, having due regard to pH, isotonicity, stability and the like, is within the skill of the art. The therapeutic compositions are also presently valuable for veterinary applications due to the lack of species specificity in factor of the T-box family due to high homology between species.

Particularly domestic animals and thoroughbred horses in addition to humans are desired patients for such treatment with the compositions of the present invention.

The therapeutic method includes administering the composition topically, systemically, or locally as an injectable and/or implant or device. When administered, the therapeutic composition for use in this invention is, of course, in a pyrogen-free, physiologically acceptable form. Further, the composition, may desirably be encapsulated or injected in a viscous form for delivery to the site of tissue damage. Therapeutically useful agents other than the proteins which may also optionally be included in the composition as described above, may alternatively or additionally, be administered simultaneously or sequentially with the composition in the methods of the invention. In addition, the compositions of the present invention may be used in conjunction with presently available treatments for cartilage injury such as cartilage allograft or autograft, in order to enhance or accelerate the healing potential of the or graft. For example, the, allograft or autograft may be soaked in the compositions of the present invention prior to implantation. It may also be possible to incorporate the protein or composition of the invention onto suture materials, for example, by freeze-drying.

The compositions may include an appropriate matrix and/or sequestering agent as a carrier. For instance, the matrix may support the composition or provide a surface for cartilage-like tissue formation. The matrix may provide slow release of the protein and/or the appropriate environment for presentation thereof. The sequestering agent may be a substance which aids in ease of administration through injection or other means, or may slow the migration of protein from the site of application.

The choice of a carrier material is based on biocompatibility, biodegradability, mechanical properties, cosmetic appearance and interface properties. The particular application of the compositions will define the appropriate formulation. Potential matrices for the compositions may be biodegradable and chemically defined. Further matrices are comprised of pure proteins or extracellular matrix components. Other potential matrices are nonbiodegradable and chemically defined. Preferred matrices include collagen-based materials, including sponges, such as Helistat.RTM. (Integra LifeSciences, Plainsboro, N.J.), or collagen in an injectable form, as well as sequestering agents, which may be biodegradable, for example hyalouronic acid derived. Biodegradable materials, such as cellulose films, or surgical meshes, may also serve as matrices. Such materials could be sutured into an injury site, or wrapped around the tendon/ligament.

Another preferred class of carrier are polymeric matrices, including polymers of poly(lactic acid), poly(glycolic acid) and copolymers of lactic acid and glycolic acid. These matrices may be in the form of a sponge, or in the form of porous particles, and may also include a sequestering agent. Suitable polymer matrices are described, for example, in WO93/00050, the disclosure of which is incorporated herein by reference.

Preferred families of sequestering agents include blood, fibrin clot and/or cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the activity of the progenitor cells.

Additional optional components useful in the practice of the subject application include, e.g. cryogenic protectors such as mannitol, sucrose, lactose, glucose, or glycine (to protect the protein from degradation during lyophilization), antimicrobial preservatives such as methyl and propyl parabens and benzyl alcohol; antioxidants such as EDTA, citrate and BHT (butylated hydroxytoluene); and surfactants sifdch as poly(sorbates) and poly(oxyethylenes); etc.

As described above, the compositions and the devices of the invention may be employed in methods for enhancing cartilage repair or for inducing cartilage formation. These methods, according to the invention, entail administering to a patient needing such tissue repair, a cell expresses at least one factor of the T-box family or in another embodiment a composition comprising an effective amount of vector comprising a nucleic acid encoding a factor of the T-box family.

In another embodiment, as described before, the composition or the cell may comprise also a vector comprising a nucleic acid encoding FGF and/or a factor of the BMP family.

Preferably the DNA molecule or protein may be injected directly into cartilage tissue such as without limitation nasal cartilage, articular cartilage etc. Therefore, the compounds of the invention may be utilised as a therapeutic agent in regard to treatment of cartilage or bone damage caused by disease or aging or by physical stress such as occurs through injury or repetitive strain, e.g. "tennis elbow" and similar complaints. The therapeutic agent of the invention may also be utilised as part of a suitable drug delivery system to a particular tissue that may be targeted.

Other therapeutic applications for the compounds of the invention may include the following: 1. Use in cartilage and/or bone renewal, regeneration or repair so as to ameliorate conditions of cartilage and/or bone breakage, degeneration, depletion or damage such as might be caused by aging, genetic or infectious disease, wear and tear, physical stress (for example, in athletes or manual labourers), accident or any other cause, in humans, livestock, domestic animals or any other animal species; 2. Stimulation of skeletal development in livestock, domestic animals or any other animal species in order to achieve increased growth for commercial or any other purpose; 3. Treatment of neoplasia or hyperplasia of bone or cartilage, in humans, livestock, domestic animals or any other animal species; 4. Suppression of growth of skeletal components in livestock, domestic animals or any other animal species in order to achieve decreased growth for commercial or any other purposes e.g. by the use of antisense molecules to the factor of the T-box family; and 5. Alteration of the quality or quantity of cartilage and/or bone for any other purpose in any animal species including humans.

Thus, according to clauses 4 and 5 the invention can be serve also for suppressing cartilage formation, by the use of an antagonist to Brachyury or to other factors of the T-box family. The antagonistic effect of dominant negative Brachyury is exemplified in Example 3. The term "antagonist" refers to a molecule which, when bound to the epitope, decreases the amount or the duration of the effect of the biological or immunological activity of epitope. Antagonists may include proteins, nucleic acids, carbohydrates, antibodies, antisense or any other molecules which decrease the effect of Brachyury or to other factors of the T-box family on cartilage formation. Such a treatment of suppression is relevant in the treatment of malignancy of the cartilage, for example without limitation in chondroma and chondrasarcoma. In another embodiment the antagonist is a dominant negative factor of the T-box family. In another embodiment the antagonist is a dominant negative Brachyury.

The term "dominant negative Brachyury refers hereinabove to Brachyury DNA binding domain (T-box, aa 1–229) without the associated regulatory domains (aa 230–436).

In another embodiment the invention provides a method of inducing chondrocyte differentiation comprising the step of administering of a recombinant vector which comprises a nucleic acid encoding a factor of the T-box family, thereby inducing chondrocyte formation. Example 2 and FIG. 2 clearly demonstrates that forced expression of the T-box factor Brachyury leads to chondrgenic development in C3H10T1/2 mesenchymal stem cells. Please note that C3H10T1/2 mesenchymal stem cells line. C3H10T1/2 stem cell line resembles human MSCs by many features including differentiation multipotentiality, high proliferation capacity and similar response to growth factors and cytokines such as BMPs.

Example 3 further strengthen the relation between Brachyury and chondrgenic development, by demonstrating that dominant negative Brachyury interferes with BMP2 dependent chondrogenic development in mesenchymal cells.

In another embodiment the invention relates to a method for the production of transplantable cartilage matrix, the method comprising the steps of: obtaining a cell; transfecting said cell with a recombinant vector comprising a nucleic acid sequence encoding a factor of the T-box family, so as to obtain an engineered cell which expresses a factor of the T-box family; and culturing said cell with the cell-associated matrix for a time effective for allowing formation of a transplantable cartilage matrix. The above method will enable the production of a cartilage matrix which will be transplanted to a subject in need when required.

In another embodiment, there is provided a method of treating a subject by ex-vivo implantation of at least one cell comprising the following steps: obtaining at least one cell from the subject; transfecting the cell with a nucleic acid which encodes at least one factor of the T-box family, so as to obtain an cell which express at least one factor of the T-box family activated cell; and administering said activated cell to the subject.

Optionally, the enriched stem cells are then expanded ex vivo by culturing them in the presence of agents that stimulate proliferation of stem cells. The culturing atep can be for example in a bioreactor which enables three dimensional growth of the cells. The enriched and optionally expanded stem cells are then infected with a vector, that expresses the at least one factor of the T-box family gene. Optionally, the vector may also carry an expressed selectable marker, in which case successfully transduced cells may be selected for the presence of the selectable marker. The transduced and optionally selected stem cells are then returned to the patient defective connective tissue and allowed to engraft themselves into the bone marrow.

One ex vivo method of enhancing repair and/or inducing formation disclosed throughout this specification comprises initially generating a recombinant viral or plasmid vector which contains a DNA sequence encoding a protein or biologically active fragment thereof. This recombinant vector is then used to infect or transfect a population of in vitro cultured connective tissue cells, resulting in a population of connective cells containing the vector. These connective tissue cells are then transplanted to a target joint space of a mammalian host, effecting subsequent expression of the protein or protein fragment within the joint space. Expression of this DNA sequence of interest is useful in substantially reducing at least one deleterious joint pathology associated with a connective tissue disorder.

It will be understood by the artisan of ordinary skill that the source of cells for treating a human patient is the patient's own connective tissue cells, such as autologous fibroblast cells. In another embodiment the source of cells can be allogenic cells which were treated so as to reduce immune response.

As used herein, a "promoter" can be any sequence of DNA that is active, and controls transcription in an eucaryotic cell. The promoter may be active in either or both eucaryotic and procaryotic cells. In another embodiment, the promoter is active in mammalian cells. The promoter may be constitutively expressed or inducible. In another embodiment, the promoter is inducible. In another embodiment, the promoter is inducible by an external stimulus. In another embodiment, the promoter is inducible by hormones or metals. Still more in another embodiment, the promoter is inducible by heavy metals. In another embodiment, the promoter is a metallothionein gene promoter. In another embodiment the promoter is inducible by antibiotics such as tetracycline. In another embodiment the promoter is inducible by a tissue specific promoter. Likewise, "enhancer elements", which also control transcription, can be inserted into the DNA vector construct, and used with the construct of the present invention to enhance the expression of the gene of interest.

In another embodiment there provided ex vivo and in vivo techniques for delivery of a DNA sequence of interest to the connective tissue cells of the mammalian host. The ex vivo technique involves culture of target connective tissue cells, in vitro transfection of the DNA sequence, DNA vector or other delivery vehicle of interest into the connective tissue cells, followed by transplantation of the modified connective tissue cells to the target joint of the mammalian host, so as to effect in vivo expression of the gene product of interest.

Alternatively, an allograft (e.g., cartilage grown in vitro from cartilage tissue removed from the patient) may be implanted by attaching a periosteum membrane (harvested, e.g., from the patient's tibia), to the bone surface and injecting the allograft beneath the membrane.

As used herein, the term "transfection" means the introduction of a nucleic acid, e.g., an expression vector, into a recipient cell by nucleic acid-mediated gene transfer.

Alternatively, the gene encoding the product of interest can be associated with liposomes and injected directly into the host, such as in the area of the joint, where the liposomes fuse with target cells, resulting in an in vivo gene transfer to the connective tissue. In another embodiment, the gene encoding the product of interest is introduced into the area of the joint as naked DNA. The naked DNA enters the target cells, resulting in an in vivo gene transfer to the cells.

The dosage of the treatment, which is the amount of the cells which express the at least one factor of the T-box family or in another embodiment the amount of the composition or the device which contain the vector comprising the nucleic acid encoding the same in the in vivo and in the ex-vivo treatment the dosage regimen will be determined by the attending physician considering various factors which modify the action of the composition, e.g., amount of bone or cartilage tissue desired to be formed, the site of the bone or cartilage damage, the condition of the damaged cartilage or bone, the size of a wound, type of damaged tissue, the patient's age, sex, and diet, the severity of any infection, time of administration and other clinical factors. The dosage may vary with the type of matrix used in the reconstitution and the types of additional proteins in the composition. The addition of other known growth factors, such as IGF-I (insulin like growth factor I), to the final composition, may also affect the dosage.

Progress can be monitored by periodic assessment of cartilage formation, and/or repair. The progress can be monitored by methods known in the art, for example, X-rays (CT), ultra-sound, MRI, arthroscopy and histomorphometric determinations.

In another embodiment, as is examplified in Example 1 the invention provides a method of screening candidate nucleic acid sequence which is involved in the early stages of cartilage development, said method comprising the step of: obtaining a cell; transfecting said cell with a vector comprising a nucleic acid sequence encoding to FGFR3; obtaining mRNA from said cell; synthesizing cDNA from said mRNA; amplifying said cDNA-hybrid, so as to obtain an amplified product; detecting said amplified product; and comparing said amplified products from said sample to amplified products derived from known samples thereby identifying candidate nucleic acid sequence which is involved in the early stages of cartilage development.

The term "involved in the early stages of cartilage development" refers hereinabove to any gene which is either upregulated on downregulated during the stage of differentiation into a cartilage cell. Such genes will enable development of drugs which will ether enhance or suppress cartilage formation or repair.

The step of "synthesizing" refer to step of building cDNA complementary to the mRNA template. As refer hereinabove and in the claims section, the step of "amplifying" refer to the selective replication of a cDNA in greater number than usual. As refer herein above and in the claims section, the step of "separating" refer to the step of separation of the products using for example, gel electrophoresis. As refer hereinabove and in the claims section, the step of "detecting" refer to the step of noticing, which is done, for example by visualization of the amplified product's bands. As refer hereinabove and in the claims section, the step of "comparing" refers to the step of searching for differences between the amplified products derived from the at least two samples. The term "RNA" refers to an oligonucleic in which the sugar is ribose, as opposed to deoxyribose in DNA. RNA is intended to include any nucleic acid, which can be entrapped by ribosomes and translated into protein. The term "mRNA" refers to messenger RNA.

RNA can be extracted from cells or tissues according to methods known in the art. In a preferred embodiment, RNA can be extracted from monolayers of mammalian cells grown in tissue culture, cells in suspension or from mammalilan tissue. RNA can be extracted from such sources by, e.g., treating the cells with proteinase K in the presence of SDS. In another embodiment, RNA is extracted by organic solvents. In yet another embodiment, RNA is extracted by differential precipitation to separate high molecular weight RNA from other nucleic acids. RNA can also be extracted from a specific cellular compartment, e.g., nucleus or the cytoplasm. In such methods, the nucleus is either isolated for purification of RNA therefrom, or the nucleus is discarded for purification of cytoplasmic RNA. Further details regarding these and other RNA extraction protocols are set forth, e.g., in Molecular Cloning A Laboratory Manual, 2nd Ed., ed. by Sambrook, Fritsch and Maniatis (Cold Spring Harbor Laboratory Press: 1989).

EXAMPLES

Experimental Procedures

DNA Constructs and Transient Transfections

For the assessment of the transcriptional activity a dimer of the double-stranded oligonucleotide of the Brachyury binding element (BBE) AATTTCACACCTAGGTGT-GAAATT (SEQ ID No: 17) (Kispert et al., 1995) was incorporated in the BamHI site before the HSV thymidine kinase minimal promoter fused to the cloramphenicol acetyltransferase (CAT)-reporter of pBLCAT5 (Boshart et al., 1992) to give reporter plasmid pBBE-CAT5. 20 h before transfection, human embryonic kidney HEK293T cells were plated at a density of $1\times10^4/cm^2$ in 6-well plates and allowed to grow under normal culture conditions. For co-transfection experiments, 250 ng per well of Brachyury expression vector and 250, 500 or 750 ng of the expression vector encoding dnBrachyury. Empty vector was added to adjust the amount of expression plasmids at 1 ug/ml. 260 ng of BBE-CAT reporter (pBBE-CAT5) was added in the presence of 140 ng of RSV-lacZ vector using the DOSPER procedure (see below). Cells were allowed to incubate for 48 h. Then, cells were collected and b-galactosidase assays were performed with the chemiluminescent b-gal reporter gene assay (Roche Diagnostics, Mannheim, Germany) and CAT-assays were carried out with the CAT ELISA kit (Roche Diagnostics, Mannheim, Germany). b-gal assay results were used to normalize the CAT assay results for transfection efficiency. All DNA transfection experiments were repeated at least three times in triplicate.

Cell Culture and Permanent Transfections

Human embryonic kidney cells HEK293T and murine C3H10T1/2 progenitor cells were routinely cultured in tissue culture flasks in Dulbecco's modified Eagle's medium supplemented with 10% heat-inactivated FCS, 0.2 mM L-glutamine, and antibiotics (50 units/ml penicillin, 50 mg/ml streptomycin). Cells were transfected using DOSPER according to the manufacturer's protocol (Roche Diagnostics, Mannheim, Germany). C3H10T1/2 cells which recombinantlly express BMP2 (C3H10T1/2-BMP2) cells were obtained by co-transfection with pSV2pac followed by selection with puromycin (2.5 ug/ml). FGFR3, Brachyury and T-box domain were PCR-amplified and cloned into expression vectors pMT7T3 and pMT7T3-pgk vectors which are under the control of the LTR of the myeloproliferative virus or of the murine phosphoglycerate kinase promoter-1, respectively (Ahrens et al., 1993). The integrity of the constructs was confirmed by sequencing. HA-tags were carboxyterminally added to full-length Brachyury and Brachyury's T-box domain by PCR with primers encoding the respective peptide sequence. Stable expression of the DNA binding T-box domain (aa 1–229) and of the dominant-negative human FGFR3 without the cytoplasmatic tyrosine kinase domains (aa 1–414) in the C3H10T1/2-BMP2 background was done by co-transfection with pAG60, conferring resistance to G418 (750 ug/ml). Individual clones were picked, propagated, and tested for recombinant FGFR3, dnFGFR3, Brachyury or T-box domain (dnBrachyury) expression by RT-PCR (see below). Selected cell clones were subcultivated in the presence of puromycine or puromycine/G418 and the selective pressure was maintained during subsequent manipulations. C3H10T1/2 cells were cultured in DMEM containing 10% fetal bovine serum. The features of C3H10T1/2-BMP2 cells have been described (Ahrens et al., 1993; Hollnagel et al., 1997; Bachner et al., 1998). For the assessment of in vitro osteo-/chondrogenic development, cells were plated at a density of $5-7.5\times10^3$ cells/cm$^2$. After reaching confluence (arbitrarily termed day 0) ascorbic acid (50 ug/ml) and 10 mM b-glycerophosphate were added as specified by Owen et al., 1990 (1990).

BMP2 Inductions

For BMP2-stimulation studies, C3H10T1/2 cells were plated at a density of $1\times10^4$ per cm$^2$ in a 9-cm culture dish. After 48 h cells were washed 3× with PBS and then cells were starved for 24 h in DMEM without serum. Before induction the medium was replaced with fresh DMEM without serum. Cells were then treated for the indicated times using recombinant BMP2 from E. coli (50 ng/ml). Cycloheximide (50 ug/ml) treatment started 30 min prior to the addition of BMP2.

RNA Preparation and RT-PCR

Total cellular RNAs were prepared by TriReagent$^{L-S}$ according to the manufacturer's protocol (Molecular Research Center Inc.). Five ug of total RNA was reverse transcribed and cDNA aliquots were subjected to PCR. RT-PCR was normalized by the transcriptional levels of HPRT. The HPRT-specific 5' and 3' primers were GCTG-GTGAAAAGGACCTCT (SEQ ID NO: 1) and AAGTA-GATGGCCACAGGACT (SEQ ID No: 2), respectively. The following 5' and 3' primers were used to evaluate osteo/chondrogenic differentiation: collagen 1a1: GCCCTGCCT-GCTTCGTG (SEQ ID No: 3), CGTAAGTTGGAATG-GTTTTT (SEQ ID No: 4); collagen 2a1: CCTGTCTGCTTCTTGTAAAAC (SEQ ID No: 5), AGCATCTGTAGGGGTCTTCT (SEQ ID No: 6); osteocalcin: GCAGACCTAGCAGACACCAT (SEQ ID No: 7), GAGCTGCTGTGACATCCATAC; (SEQ ID No: 8); PTH/PTHrP-receptor: GTTGCCATCATATACTGTTTCTGC (SEQ ID No: 9), GGCTTCTTGGTCCATCTGTCC (SEQ ID No: 10); FGFR3: CCTGCGCAGTCCCCCAAAGAAG (SEQ ID No: 11); CTGCAGGCATCAAAGGAGTAGT (SEQ ID No: 12); FGFR2: TTGGAGGATGGGCCGGT-GTGGTG (SEQ ID No: 13), GCGCTTCATCTGCCTG-GTCTTG (SEQ ID No: 14). The primer pairs for Brachyury and Sox9 have been described in (Johansson and Wiles, 1995) and (Zehentner et al., 1999), respectively. Vector-borne transcripts for Brachyury were evaluated with nested primers sets with either vector specific 5'- or 3'-primers: TTAGTCTTTTTGTCTTTTATTTCA (SEQ ID No: 15); GATCGAAGCTCAATTAACCCTCAC(SEQ ID No: 16).

Western Blotting

Recombinant cells from petri dishes (13.6 cm diameter) were harvested at different time points before (day B2), at (day 0) and after (days 2, 4, 7) confluence. Lysis was in RIPA buffer (1% (v/v) nonidet P-40, 0.1% SDS (w/v), 0.5% sodium deoxycholate in PBS, containing 100 ug/ml PMSF, 2 ug/ml aprotinin, and 1 mM Na$_3$VO$_4$). Lysates were centrifuged (30 min, 10.000 g, 4 C) and the supernatants were stored at −70 C until analysis. Protein concentration of the lysates was determined using coomassie brilliant blue. Protein was precipitated with ethanol, resuspended in reducing (containing DTT) or non-reducing sample buffer and subjected to SDS-gel electrophoresis in 12.5% T polyacrylamide gels (20 ug/lane). Proteins were transferred to nitrocellulose membranes by semidry-blotting. Protein transfer was checked by staining of the membranes with Ponceau S. After blocking, membranes were incubated incubated overnight at 4 C with a polyclonal antibody to the HA-tag (SC-805, Santa Cruz Biotechnology, Santa Cruz, Calif.)

diluted 1:200 in blocking solution. FGFR3 and FGFR2 antibodies were from Santa Cruz Biotechnology (#SC-123, #SC-122; Santa Cruz, Calif.). The secondary antibody (Dianova, Hamburg) was applied at 1:5000 in blocking solution for 2 h at room temperature. Color development was performed with 4-chloro-1-naphthol and $H_2O_2$.

Histological Methods and Verification of Cellular Phenotypes

Osteoblasts exhibit stellate morphology displaying high levels of alkaline phosphatase, which was visualized by cellular staining with SIGMA FAST BCIP/NBT (Sigma, St. Louis, Mo.). Proteoglycan secreting chondrocytes were identified by staining with Alcian Blue at pH 2.5 and staining with Safranin O (Sigma, St. Louis, Mo.). For collagen-immunohistochemistry cells were washed with PBS and fixed with methanol for 15 min at −20 C by methanol. Primary antibodies were diluted with 1% goat serum in PBS. Monoclonal anti-collagen II antibodies (Quartett Immunodiagnostika, Berlin, Germany, # 031502101) were diluted 1:50 and monoclonal anti-collagen X antibodies (Quartett Immunodiagnostika, Berlin, Germany, # 031501005) 1:10, respectively. Incubation was for 1 hour at room temperature followed by staining with Zymed HistoStain SP kit (Zymed Laboratories Inc., San Francisco, Calif.) applying the manufacturer's protocol. A positive signal is indicated by a red color precipitate of AEC (aminnoethylcarbazole).

In Vivo Transplantation

Before in vivo transplantation, aliquots of $2-3\times10^6$ cells were mounted on individual type I collagen sponges (Colastat[7] #CP-3n, Vitaphore Corp., 2×2×4 mm.) and transplanted into the abdominal muscle of female nude mice (4–8 weeks old). Before transplantation animals were anaesthetized with ketamine-xylazine mixture 30 ul/per mouse i.p. and injected i.p. with 5 mg/mouse of Cefamzolin (Cefamezin[7], TEVA). Skin was swabbed with chlorhexidine gluconate 0.5%, cut in the middle abdominal area, an intramuscular pocket was formed in a rectal abdominal muscle and filled with the collagen sponge containing cells. Skin was sutured with surgical clips. For the detection of engrafted C3H10T1/2 cells the mice were sacrificed 10 days and at 20 days after transplantation. Operated transplants were fixed in 4% paraformaldehyde cryoprotected with 5% sucrose overnight, embedded, and frozen. Sections were prepared with a cryostat (Bright, model OTF) and stained with H&E, Alcian Blue and Safranin O.

RNA-In Situ-Hybridization

Embryos were isolated from pregnant NMRI mice at day 18.5 post conceptionem (dpc). The embryos were fixed overnight with 4% paraformaldehyde in PBS at 4 C. 10 um cryosections were mounted on aminopropyltriethoxysilane coated slides and non-radioactive RNA-in situ-hybridizations were done as described (Bächner et al., 1998) and by following the instructions of the manufacturer (Roche, Mannheim). In short: For hybridization sense- and antisense RNA probes from a 1.8 kb murine Brachyury cDNA was used. For the generation of collagen 1a1 or collagen 2a1 the vector pMT7T3 was used harbouring specific probes (Metsäranta et al., 1991). Hybridization was performed with 0.5–2 ug denatured riboprobe/ml) over night at 65 C in a humid chamber. For digoxygenin (DIG)-detection slides were blocked in 5xSSC, 0.1% Triton, 20% FCS for 30 minutes following two washes with DIG-buffer 1 (100 mM Tris, 150 mM NaCl, pH 7.6) for 10 minutes. Slides were incubated in anti-DIG-alkaline phosphatase coupled antibodies diluted 1:500 in DIG-buffer 1 over night in a humid chamber. Slides were washes with 0.1% Triton in DIG-buffer 1 for 2 hours with several changes of the washing solution and equilibrated in DIG-buffer 2 (100 mM Tris, 100 mM NaCl, 50 mM $MgCl_2$). Detection was performed using BM-purple substrate (Roche, Mannheim) in DIG-buffer 2 with 1 mM Levamisole for 1–6 hours depending on the probe. Reaction was stopped in TE-buffer and slides were incubated in 3% paraformaldehyde in PBS for 3 minutes, in 0.1 M glycine in PBS for 3 minutes and washed three times in PBS for 3 minutes. Slides were counterstained with 0.5% methylenegreen in PBS for 1 minute, dehydrated in graded alcohol series, air dried and mounted with Eukitt.

Experimental Results

Example 1

BMP2-Dependent Chondrogenic Development in C3H10T1/2 MSCs Involves FGF-Receptor 3

During a substractive screen for BMP-regulated genes in recombinant BMP2-expressing C3H10T1/2 (C3H10T1/2-BMP2) cells upregulation of the Fibroblast Growth Factor Receptors 3 and 2 (FGFR3, FGFR2) was noted at both the transcriptional and protein levels (FIGS. 1$a$, $c$, respectively). These two receptor types exhibit different induction kinetics. FGFR3 is upregulated during early stages of cultivation in the stable C3H10T1/2-BMP2 line while FGFR2 shows a delayed response (FIGS. 1$a$, $c$). The fast upregulation of FGFR3 seems to be due to an immediate response to BMP2 since exogenously-added BMP2 mediated FGFR3 transcription in wild-type C3H10T1/2 cells in the presence of cycloheximide (FIG. 1$b$). In contrast to FGFR3 and FGFR2 is FGFR1 constitutivelly expressed in wild type and C3H10T1/2-BMP2 cells (FIG. 1$a$) while FGFR4 does not show any significant rates of expression (data not shown). Since FGFs and their receptors are crucial modulators of chondrogenic development, an assessment of whether the immediate BMP2-dependent upregulation of FGFR3 in C3H10T1/2 is involved in the onset of chondrogenic differentiation was conducted. Indeed the results demonstrated that forced expression of the wild-type FGFR3 (FGFR3$^{WT}$) was sufficient for the development of morphologically distinct chondrocytes in C3H10T1/2-FGFR3$^{WT}$ cells (FIGS. 1$d$, $e$). Moreover, the constitutively active mutant FGFR3 (Ach, G380R) possesses the same capacity (data not shown). The forced expression of FGFR3$^{WT}$ in MSCs stimulates MAPK signaling in these cells as documented by enhanced levels of ERK1 and ERK2 phosphorylation (right panels in FIG. 1$d$), leads to the development of histologically distinct chondrocytes and induces or increases expression of chondrogenic marker genes such as collagen 2a1, the PTH/PTHrP receptor and transcription factor Sox9 (FIG. 1$e$). In C3H10T1/2 cells Sox9 is already expressed at substantial levels that are further upregulated by BMP2- and FGFR3 which is consistent with recent observations (FIG. 1$e$) (Zehentner et al., 1999; Murakami et al., 2000).

The immediate BMP2-dependent upregulation of FGFR3 in MSCs (C3H10T1/2) and the inherent capacity of this receptor to initiate chondrogenic development in these cells prompted a screen for FGFR3-regulated transcription factors. It was observed that among the transcription factors tested, the T-box transcription factor Brachyury was upregulated in FGFR3-expressing C3H10T1/2 cells (see also FIG. 5$a$). Thereupon, the chondrogenic potential that Brachyury possesses after recombinant expression in wild-type C3H10T1/2 cells (see below) has been hypothesized.

Example 2

Figure 2A:
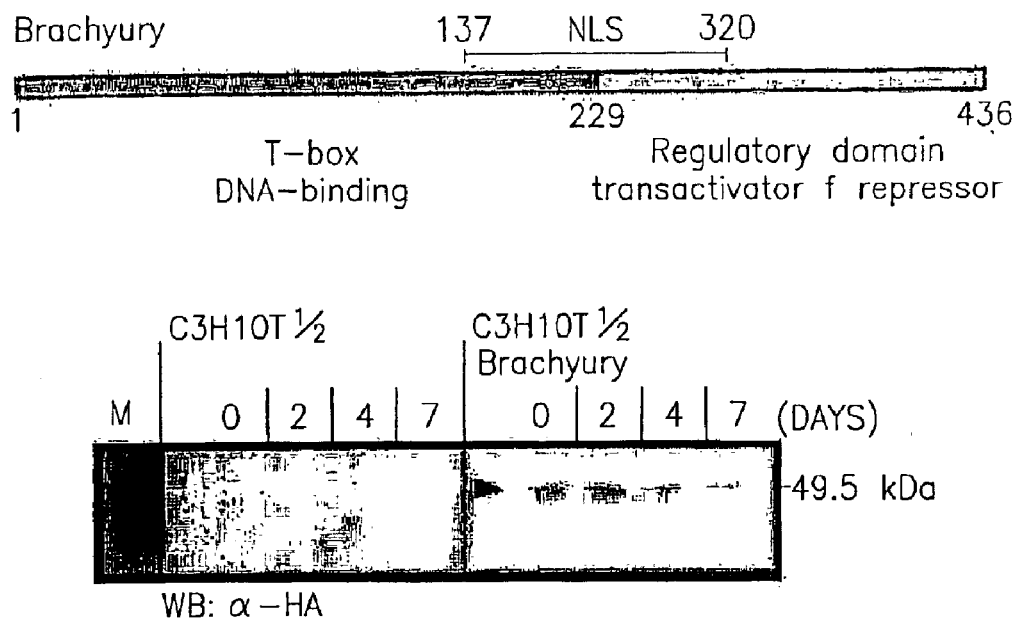
FIG. 2a upper panel: schematic representation of Brachyury according to Kispert et al., 1995 (1995).
Figure 2B:
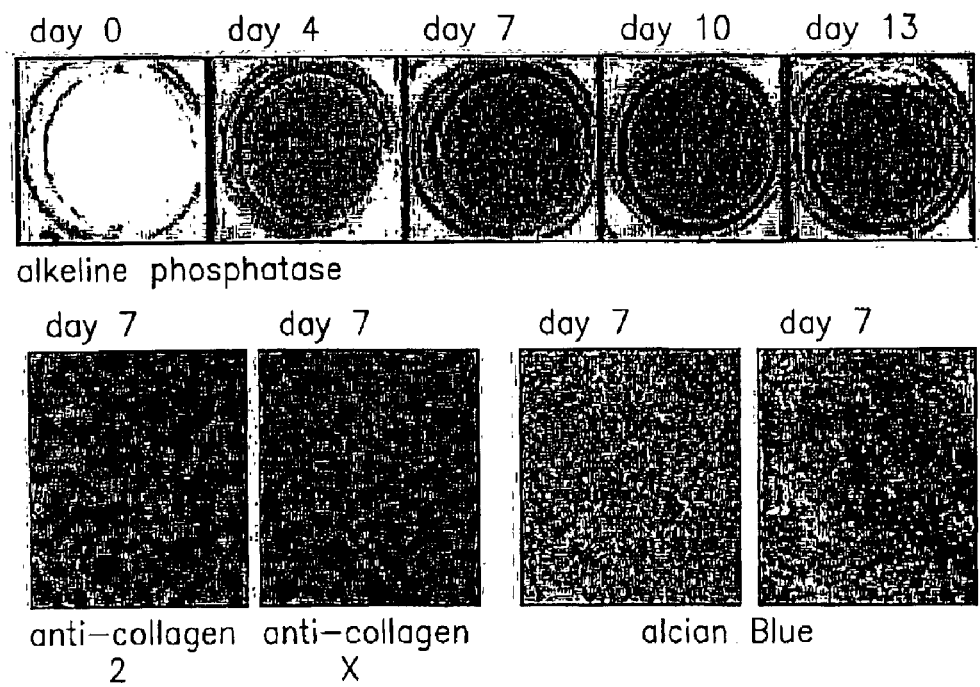
FIG. 2b shows the histological characterization of C3H10T1/2-Brachyury cells in culture. Upper panel: at day 4 post-confluency cells develop alkaline-phosphatase positive osteoblast-like cells. Lower right panel: Alcian Blue histology of C3H10T1/2 cells stably expressing Brachyury indicative for secreted proteoglycans and efficient differentiation into the chondrogenic lineage. Lower left panel: Collagen-immunohistochemistry of C3H10T1/2-Brachyury cells in culture 7 days post-confluency.
Figure 2C:
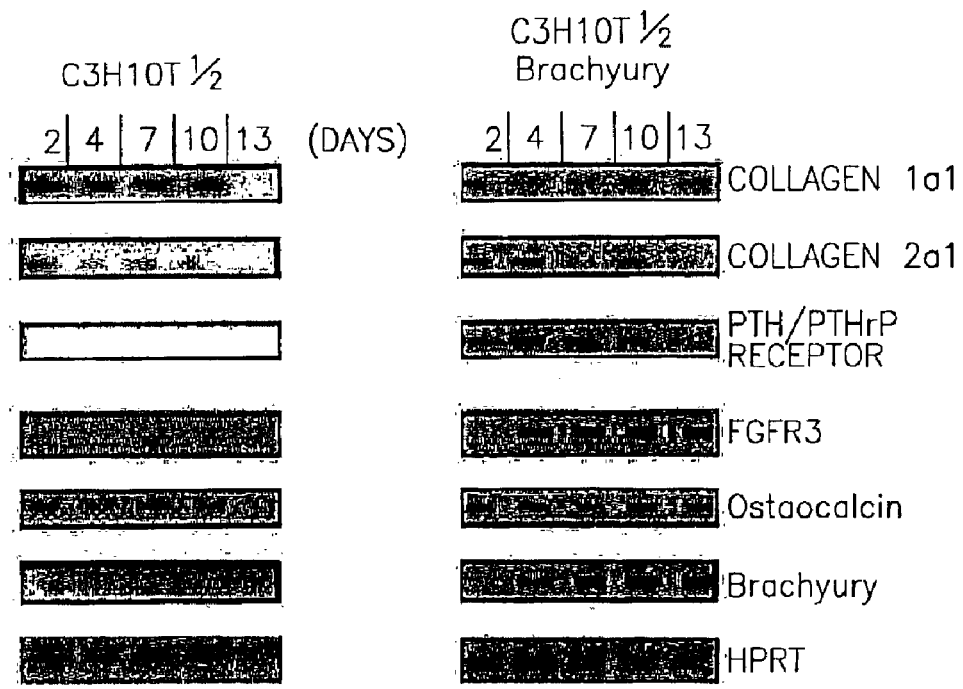
FIG. 2c shows the RT-PCR analysis of the expression of chondrogenic and osteogenic marker genes in C3H10T1/2 cells recombinantlly-expressing Brachyury.
Figure 2D:
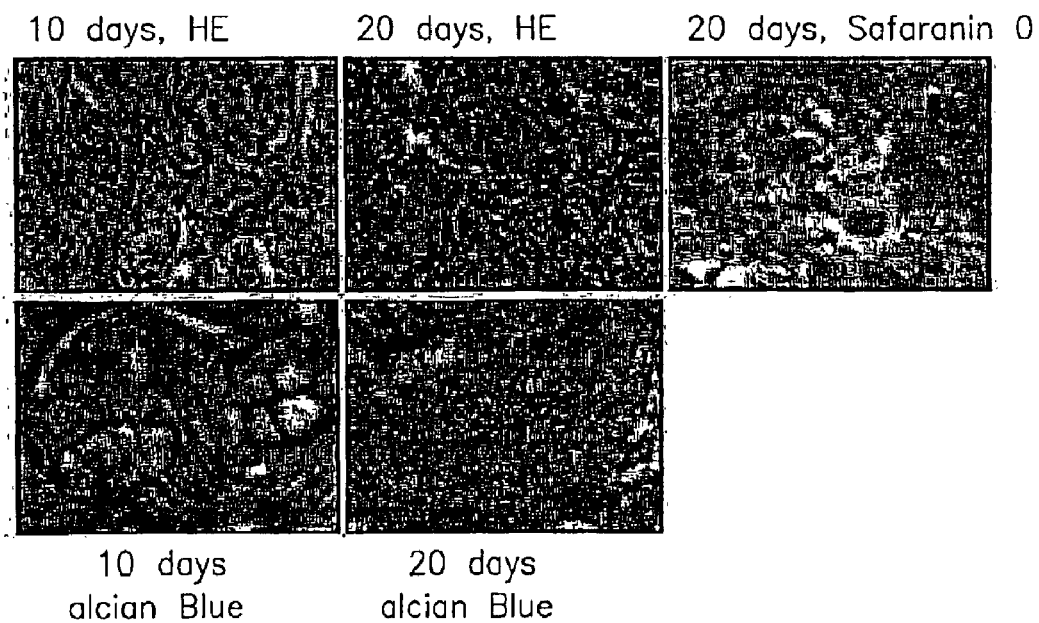
FIG. 2d shows the forced expression of the T-box factor Brachyury in C3H10T1/2 cells which leads to differentiation into chondrocytes and cartilage development at murine ectopic sites after intramuscular transplantation.

Forced Expression of the T-box Factor Brachyury Leads to Chondrogenic Development in C3H10T1/2 Mesenchymal Stem Cells Brachyury has originally been described as the first member of a family of transcription factors that harbors a T-box as the DNA-binding domain. In order to assess whether the FGFR3-dependent upregulation of the T-box factor Brachyury in C3H10T1/2 might play a role in chondrogenesis Brachyury cDNA was expressed under the control of the murine phosphoglycerate kinase-1 (PGK-1) in mesenchymal stem cell line C3H10T1/2 to allow moderate expression levels of Brachyury (C3H10T1/2-Brachyury). The recombinant expression of Brachyury cDNA under the control of the murine phosphoglycerate kinase-1 (PGK-1) in MSCs (FIG. 2a) gave rise to efficient chondrogenic differentiation resulting in alkaline phosphatase positive cells (beginning at day 4) and Alcian Blue positive chondrocyte-like cells (at day 10 post-confluence; FIG. 2b). Three individual C3H10T1/2 clones were investigated in regard to their chondrogenic potential and gave similar results. Immunohistochemistry confirms the presence of the chondrocyte-specific collagen 2 but not of collagen X which is typical for late stages of chondrocytic differentiation (hypertophic chondrocytes) (FIG. 2b, left panel). Major marker genes of chondrogenic and, also, of osteogenic development show a transient (collagen 2a1, PTH/PTHrP-receptor) or permanent upregulation (osteocalcin gene and the chondrogenic transcription factor Sox9) in C3H10T1/2-Brachyury in comparison with C3H10T1/2 cells which were stably transfected with an empty expression vector (FIG. 2c). Although, the induction of the osteocalcin gene indicates an osteogenic potential for C3H10T1/2-Brachyury, ectopic transplantation of these cells in murine intramuscular sites results exclusively in the massive formation of proliferating chondrocytes and cartilage (FIG. 2d). These ectopic transplantations have been performed three times and in all cases these transplants developed chondrocytes and cartilage. After both 10 and 20 days transplants exhibit a histological presence of proteoglycans (Alcian Blue, Safranin O) while bony elements or mineralized particles are not observed (FIG. 2d). After 20 days the ectopic implants show areas of extensive extracellular matrix production as visualized by histological analyses (FIG. 2d). The use of stronger viral promoters such as the LTR of the myeloproliferative virus (MATERIALS and METHODS) resulted in increased cellular proliferation without the apparent formation of histologically distinct mesenchymal cell types (not shown).

Example 3

Dominant-Negative Brachyury Interferes with BMP2-Dependent Chondrogenic Development in MSCs.

Figure 3A:
FIG. 3a shows that Brachyury's T-box domain interferes with the transcriptional activity of full-length Brachyury.
Figure 3A:
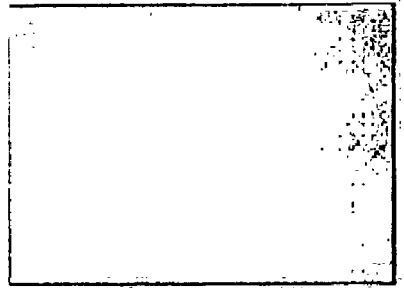
Figure 3A:
Figure 3A:
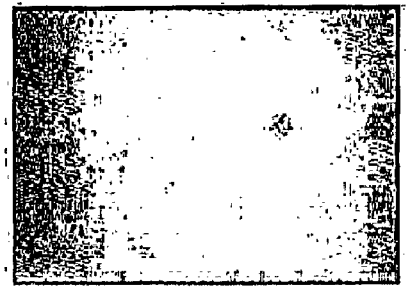

It was expected that Brachyury's DNA-binding domain (T-box, aa 1–229) without the associated regulatory domains (aa 230–436) should dominant-negatively (dn) interfere with endogenous Brachyury-mediated events in C3H10T1/2-BMP2 cells. A partial nuclear localization signal (NLS) which has been attributed to the T-box domain should allow a substantial nuclear accumulation (Kispert et al., 1995). The dominant-negative nature of the T-box domain was confirmed in DNA co-transfection assays performed in HEK293 T cells. This particular cell lines was used because expression levels are in general considerably higher in these cells than in C3H10T1/2. This cell line does not express Brachyury (data not shown). Exogenous Brachyury trans-activated a construct containing two copies of the consensus Brachyury binding element (BBE) oligonucleotide fused to a minimal HSV thymidine kinase (TK)-minimal promoter-CAT chimeric gene, pBBE(2x)-CAT5 (FIG. 3a). Indeed, co-transfection of pBBE(2x)-CAT5 with a recombinant Brachyury-expressing vector resulted in a 25-fold activation, whereas an empty expression vector had no effect (FIG. 3a). Co-transfection of full-length Brachyury (Brachyury wt) with increasing amounts of an expression vector expressing the T-box domain (dnbrachyury) (1:1, 1:2, 1:3) led to a clear decrease in CAT (7-fold). Exogenous dnBrachyury alone transactivated pBBE(2x)-CAT5 (BBE) only 3-fold.

Figure 3B:
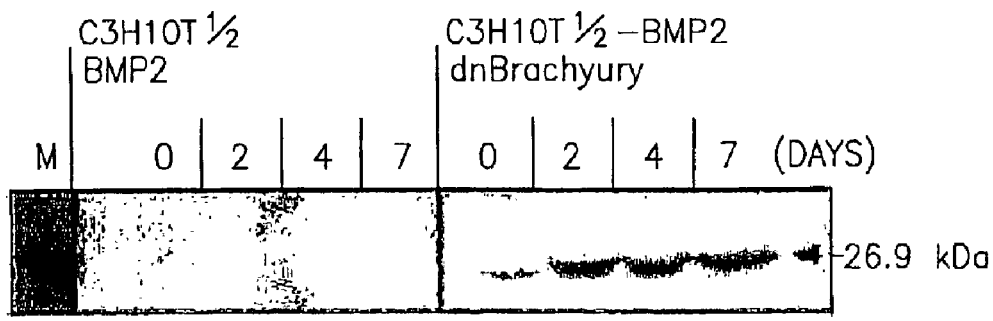
FIG. 3b shows expression of dnBrachyury (T-box domain) in C3H10T1/2-BMP2 during cultivation (day 0; cellular confluence) The T-box domain (aa 1–229) has been subcloned and HA-tagged in expression vector pMT7T3 and constitutively expressed in C3H10T1/2-BMP2 cells. The recombinantlly expressed T-box domain (dnBrachyury) is indicated (triangle).
Figure 3C:
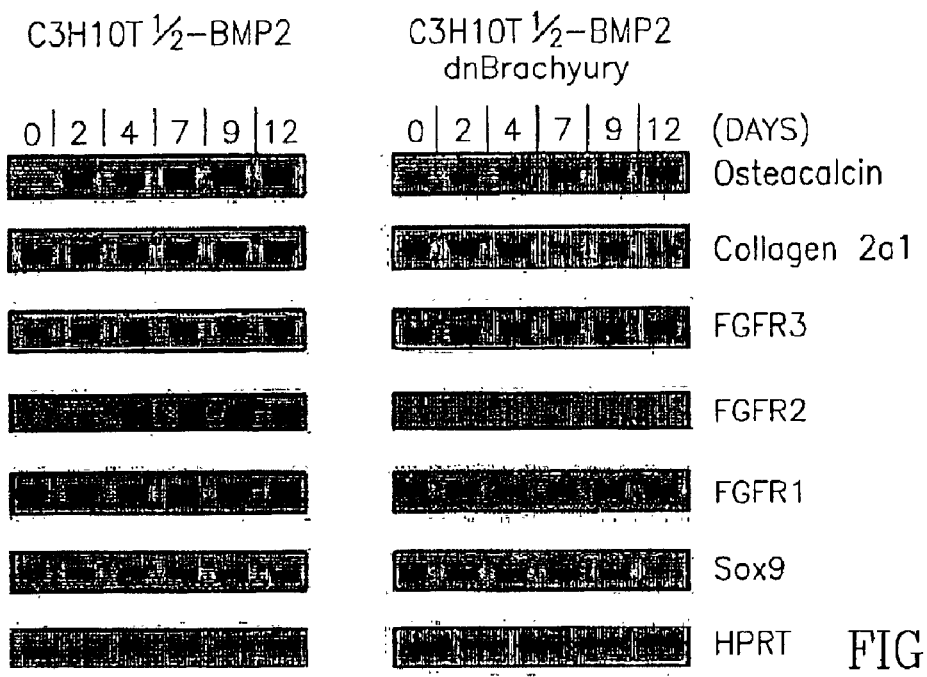
FIG. 3c demonstrates RT-PCR experiments with osteo-/chondrogenic marker genes show that T-box domain (dnBrachyury) expression in C3H10T1/2-BMP2 cells interferes with the BMP2 dependent of FGFR2 but not FGFR3 expression.
Figure 3D:
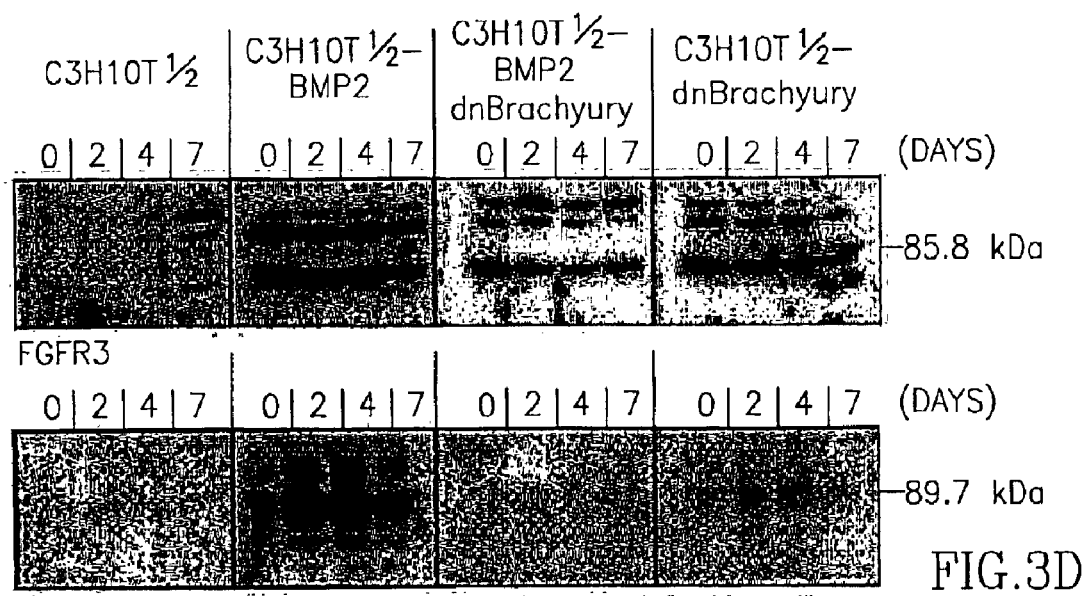
FIG. 3d shows that dnBrachyury (T-box) interferes with BMP2-mediated FGFR2 expression as analyzed by western immunoblotting with antiFGFR3 and antiFGFR2 antibodies as described FIG. 1.
Figure 3E:
FIG. 3e shows the forced expression of the dominant-negative acting T-box domain in C3H10T1/2-BMP2 cells interferes with BMP-2 mediated osteo-/chondrogenic development.

The forced expression of the HA-tagged T-box domain (dnbrachyury) is observed throughout in vitro cultivation (FIG. 3b) and strongly interfered with the BMP2-mediated formation of alkaline phosphatase positive osteoblast-like and Alcian Blue chondrocyte-like cells in vitro (FIG. 3e). In vivo, in ectopic transplantations of C3H10T1/2-BMP2 in intramuscular sites, dnBrachyury allowed the development of connective tissue only (FIG. 3e). In addition, the chondrocyte-specific collagen 2a1 mRNA levels are more sensitive to the presence of dnBrachyury than mRNA levels of the distinct osteogenic marker osteocalcin. The latter is hardly affected, consistent with the idea that Brachyury possesses a predominant chondrogenic capacity in this particular cell type. Interestingly, the BMP2-mediated transcriptional upregulation of FGFR3 in C3H10T1/2 is not obstructed by dnBrachyury indicating that the immediate BMP2-mediated FGFR3 induction is independent of Brachyury or other T-Box factors (FIGS. 3c, d). However, FGFR2-expression which exhibits a delayed response in C3H10T1/2-BMP2 cells (FIGS. 1 and 3) displays a high sensitivity to dnBrachyury. BMP-mediated FGFR2 expression is almost completely suppressed by the dominant-negative acting T-box domain (FIGS. 3c, d). This may indicate that that the presence of FGFR2 seems necessary for the osteo-/chondrogenic differentiation in this mesenchymal progenitor line (FIGS. 3c, d).

Figure 4A:
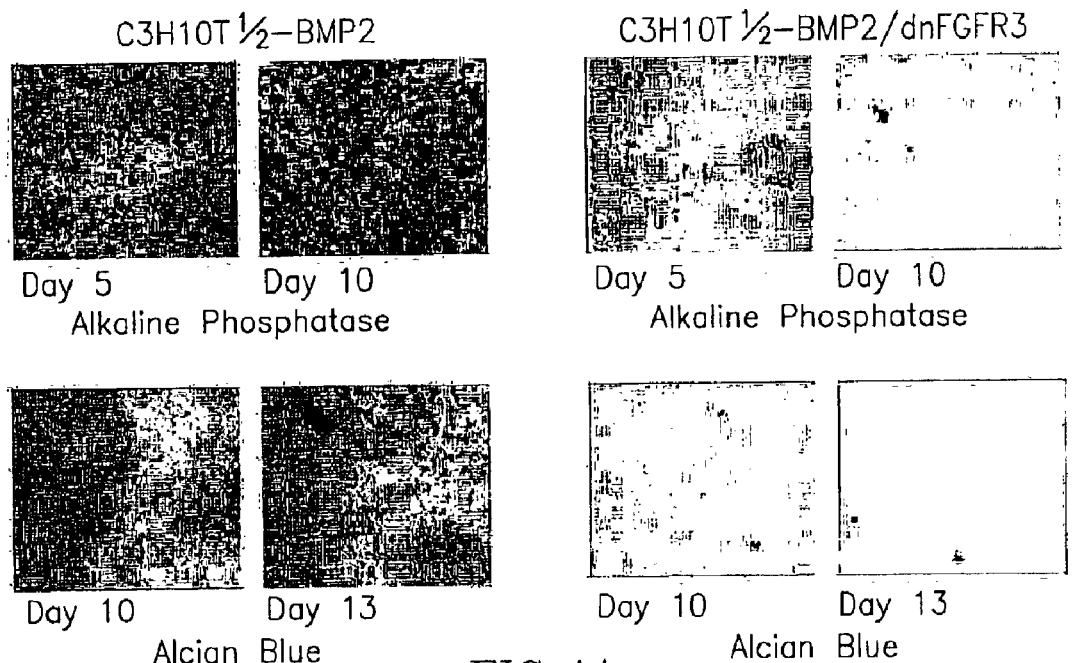
FIG. 4a shows that forced expression of dnFGFR3 in C3H10T1/2-BMP2 cells interferes with BMP-2 mediated development of alkaline phosphatase positive and Alcian Blue positive chondrocyte-like cells, respectively.
Figure 4B:
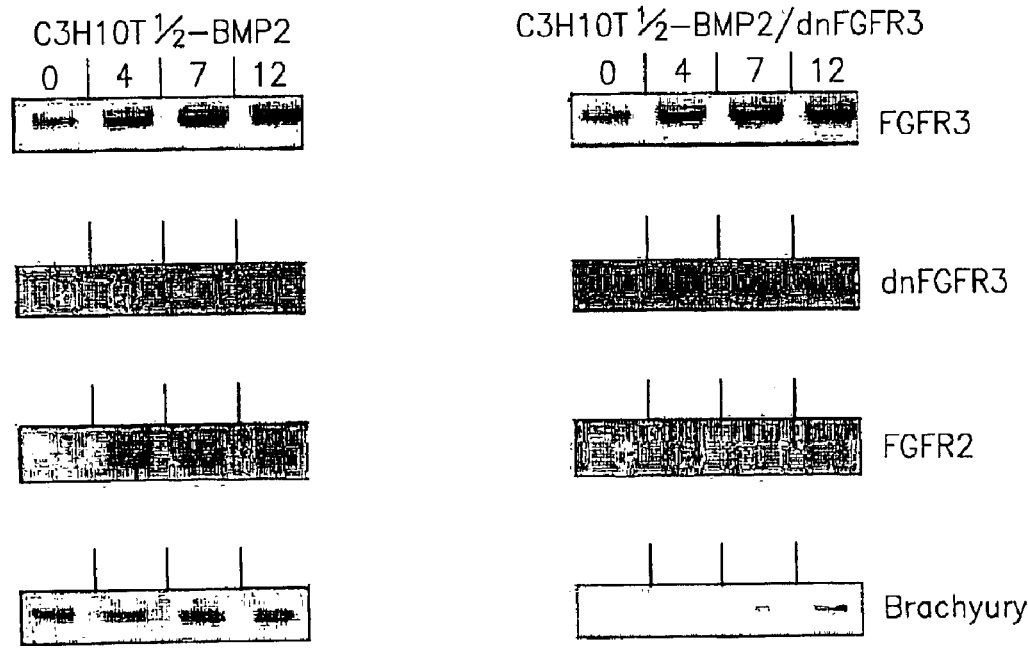
FIG. 4b shows that dnFGFR3 interferes with BMP2-dependent FGFR2 and Brachyury but not with FGFR3 expression in C3H10T1/2-BMP2 cells.
Figure 7:
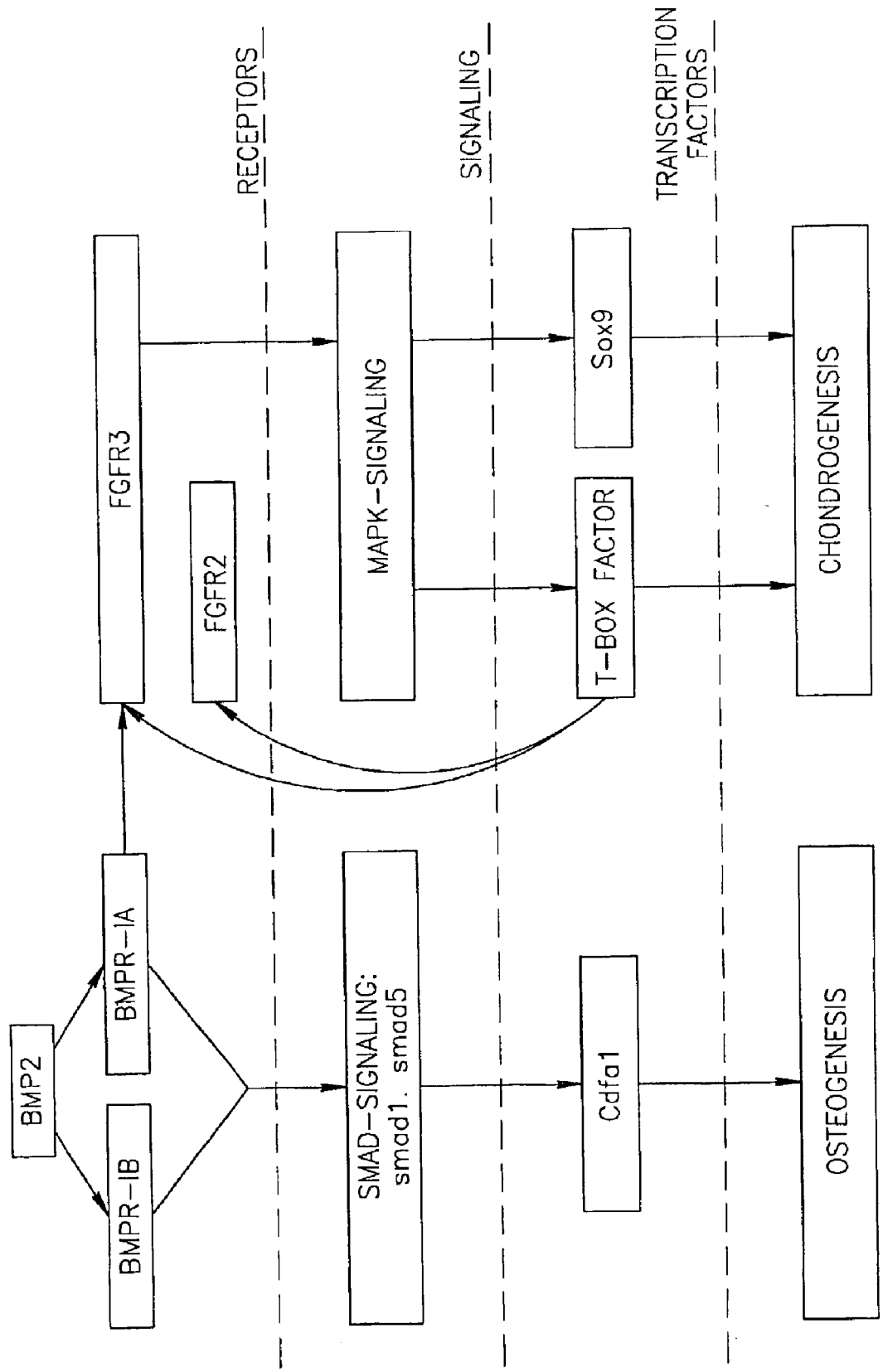
FIG. 7. Model of BMP2-dependent osteo-/chondrogenic development in mesenchymal stem cells.

Furthermore, this suggests a hierarchy of FGFR-mediated signaling for chondrogenic development. FGFR3-dependent signaling is induced at first by BMP2 and as a consequence, FGFR2 mediated signaling becomes active. Such a model is proposed in FIG. 7. This model predicts that a forced expression of dominant-negative FGFR3 would interfere with BMP2-mediated chondrogenesis and with FGFR2 and Brachyury expression. Indeed, an FGFR3-variant without the cytoplasmatic tyrosine-kinase domains downregulates BMP2-dependent mRNA expression levels of FGFR2 and Brachyury (FIG. 4b) and interferes with the histological manifestation of alkaline phosphatase or Alcian Blue positive chondrocyte-like cells (FIG. 4a).

Example 4

Figures 5A, 5B:
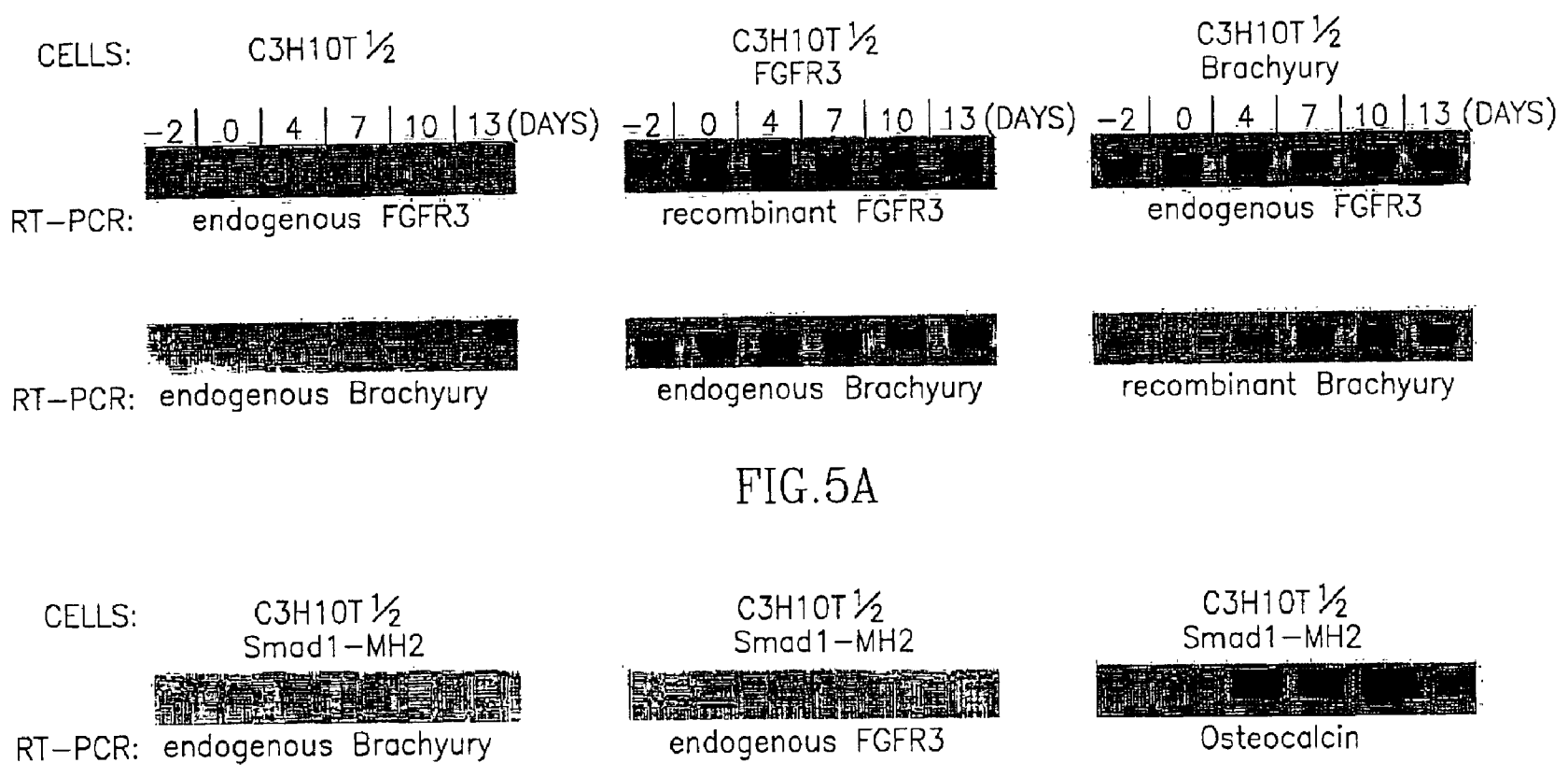

FGFR3 and the T-box Factor Brachyury Are Involved in an Autoregulatory Loop for Chondrogenic Development in C3H10T1/2 Progenitors During amphibian gastrulation, mesodermal Brachyury is involved in an autoregulatory loop with FGF that is present in the embryo (1998). In C3H10T1/2 cells several FGF genes tested (FGF2, 4, and 9) were not Brachyury- or FGFR3-regulated (data not shown) and, therefore, are unlikely members of such a loop. However, a loop seems to exist between FGFR3 and Brachyury since forced expression of either one lead to the induction of the other one in C3H10T1/2 (FIG. 5a). These experiments indicate that after BMP2-mediated initiation of the chondrogenic lineage, the chondrogenic differentiation may advance for some time in a BMP2-independent fashion maintained by the autoregulatory loop between FGFRs and FGF-regulated transcription factors such as the T-box factor Brachyury.

In a preceding study it was shown that BMP-mediated R-Smad signaling alone is not sufficient for cartilage development in C3H10T1/2 cells. Thereby, forced expression of Smad1 or the biologically active Smad1-MH2 domain is able to mimic BMP2-mediated onset of osteogenic differentiation (Takeuchi et al., 2000). However, in contrast to osteogenic marker genes such as the osteocalcin gene, Smad1-MH2 domain-signaling is not sufficient to mimic BMP2-dependent FGFR3- and the concomitant Brachyury-gene induction (FIG. 5b). Other BMP-activated R-Smads such as Smad5 and Smad8 are also unable to mediate or to mimic BMP2-dependent FGFR3-induction in C3H10T1/2 cells (data not shown) indicating R-Smad-MH2-independent pathways for FGFR3 induction or, alternatively, cooperative activities of R-Smads with other transcription factors (Mazars et al., 2000).

Example 5

Figure 6A:
FIG. 6. Brachyury is expressed at skeletal sites during late murine embryonic development (18.5 dpc). Comparative expression analysis of murine Brachyury (Bra), Collagen 1a1 (Col 1a1) and Collagen 2a1 (Col 2a1) in embryonic development 18.5 dpc. a, Intervertebral discs development. Consecutive sagittal (a–g) and transversal (h–j) sections of 18.5 dpc mouse embryos were hybridized with riboprobes as indicated. Expression of Brachyury is enhanced in the nucleus pulposus (a, d), Col 1a1 in the outer annulus (arrowheads in b, e), and Col 2a1 in the cartilage primordium of the vertebrae (c,f). No signals are obtained using RNase pre-incubated sections (g). With transversal sections at the level of the upper lumbar vertebra expression of Brachyury is in addition detectable in distinct cells of the neural arch (h) whereas Col 1a1 is expressed in the outer annulus (i) and Col 2a1 in the cartilage primordium (j). b, Limb bud development. Consecutive transversal sections of a 18.5 dpc mouse hind limb at the level of the metatarsals hybridized with riboprobes as indicated. Expression of Brachyury is evident in distinct chondrogenic cells of the forming metatarsal bones (a), better visible with higher magnification (b,c). In contrast Col 1a1 is expressed in the outer periosteal layer (d–f) and Col 2a1 expression is enhanced in differentiating chondrocytes (g–i). As it was evident for the intervertebral disc formation expression of Brachyury is only evident in chondrocyte-like cells that do not express Col 2a1. ch, chondrocytes; cp, cartilage primordium; mta, metatarsal; np, nucleus pulposus; oa, outer annulus; pl, periosteal layer; sk, skin bar, 100□m.
Figure 6B:
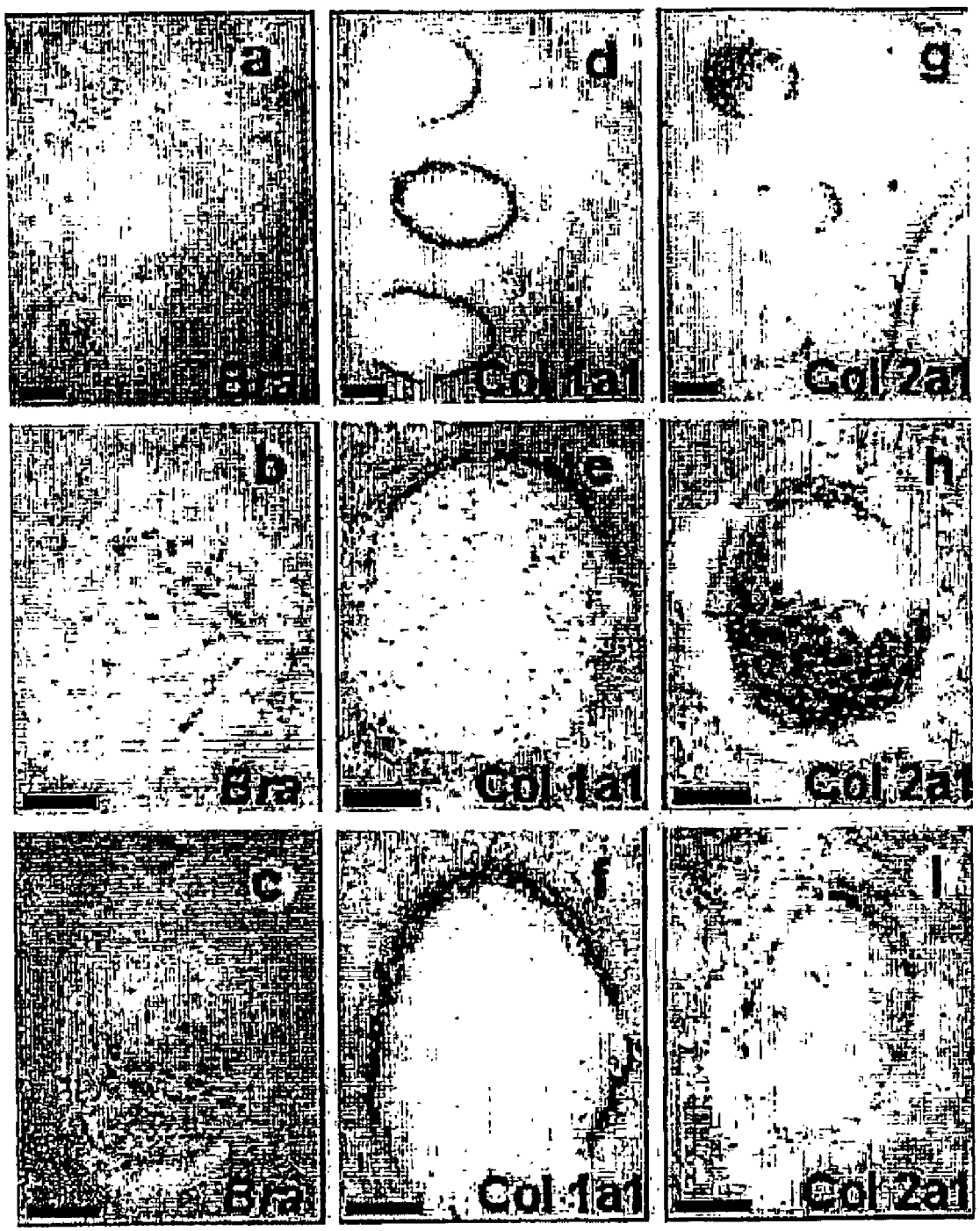

The T-box Factor Brachyury Is Expressed in Maturing Cartilage During Murine Embryonic Development The rule of Brachyury skeletogenesis in vivo was also assessed. Brachyury is expressed at high levels early in vertebrate embryonic development and is involved in gastrulation and in the dose-dependent determination of mesodermal cell fates (see INTRODUCTION, DISCUSSION). After gastrulation, Brachyury-expression is downregulated and persists in the notochord to the end of embryogenesis (Kispert and Herrmann, 1994). Comparative mRNA expression analysis of murine Brachyury (Bra), collagen 1a1 (col 1a1) and collagen 2a1 (col 2a1) in skeletal development (18.5 dpc) indicates that Brachyury is expressed at significant levels in cartilage forming cells of the intervertebral disks and in limb bud development (FIG. 6). Expression of Brachyury is enhanced in intervertebral disc development in the nucleus pulposus in 18.5 dpc mouse embryos (FIGS. 6A, a, d) confirming earlier reports (Wilkinson et al., 1990). Collagen 1a1 is expressed in the outer annulus (arrowheads in FIGS. 6A b, e), and collagen 2a1 in the cartilage primordium of the vertebrae (FIGS. 6A, c, f). In transversal sections made at the level of the upper lumbar vertebra, expression of Brachyury is in addition detectable in distinct chondrogenic cells of the neural arch (FIGS. 6A, h) whereas collagen 1a1 expression is maintained in the outer annulus (FIGS. 6A, i), as is collagen 2a1 in the cartilage primordium (FIGS. 6A, j). In murine limb bud development (18.5 dpc; hind limb) expression of Brachyury is evident in distinct chondrogenic cells of the forming metatarsal bones (FIGS. 6B, a–c). In contrast, collagen 1a1 is expressed in the outer periosteal layer (FIGS. 6B, d–f) and collagen 2a1 expression is enhanced in differentiating chondrocytes (FIGS. 6B, g–i). Interestingly, like in intervertebral disc formation, the expression of Brachyury is only evident in chondrocyte-like cells that do not express Col 2a1 indicating that Brachyury expression is upregulated in chondrogenic cells before or after collagen 2 expression.

---

What is claimed is:

1. A method of repairing or forming a cartilage in a subject comprising the steps of:

obtaining a mesenchymal stem cell from the subject;

transfection said mesenchymal stem cell with a recombinant vector comprising a nucleic acid sequence encoding a Brachyury protein, so as to obtain an engineered cell which expresses a Brachyury protein; and administering said engineered cell to the subject at a site of cartilage damage in the subject, wherein said engineered cell differentiates into chondrocytes and thereby repairing or forming cartilage in the subject.

2. The method of claim 1, wherein said cell further expresses a factor which upregulates expression of the Brachyury protein.

3. The method of claim 2, wherein said factor which upregulates expression of the Brachyury protein is FGF or BMP2.

4. The method of claim 1, wherein said method further comprises administering a recombinant vector which comprises a nucleic acid encoding a factor which upregulates expression of the Brachyury protein.

5. The method of claim 4, wherein said factor which upregulates expression of the Brachyury protein is FGF or BMP2.

6. A composition comprising an isolated, engineered mesenchymal stem cell which expresses a Brachyury protein and a pharmaceutically acceptable carrier.

7. The composition of claim 6, wherein said mesenchymal stem cell further expresses a factor which upregulates expression of the Brachyury protein.

8. The composition of claim 7, wherein said factor which upregulates expression of the Brachyury protein is FGF or BMP2.

9. The composition of claim 7, wherein said composition is a pharmaceutical composition.

* * * * *